(12) United States Patent
Panigrahi et al.

(10) Patent No.: US 6,845,326 B1
(45) Date of Patent: Jan. 18, 2005

(54) OPTICAL SENSOR FOR ANALYZING A STREAM OF AN AGRICULTURAL PRODUCT TO DETERMINE ITS CONSTITUENTS

(75) Inventors: Suranjan Panigrahi, Fargo, ND (US); Guangjun Zhang, Beijing (CN)

(73) Assignee: NDSU Research Foundation, Fargo, ND (US)

(*) Notice: Subject to any disclaimer, the term of this patent is extended or adjusted under 35 U.S.C. 154(b) by 600 days.

(21) Appl. No.: 09/706,747

(22) Filed: Nov. 7, 2000

Related U.S. Application Data

(60) Provisional application No. 60/175,636, filed on Jan. 12, 2000, and provisional application No. 60/164,161, filed on Nov. 8, 1999.

(51) Int. Cl.[7] ............................................. G06F 19/00
(52) U.S. Cl. ........................... 702/22; 702/33; 702/40; 702/49; 702/134; 250/339.02; 250/339.12; 250/339.11; 356/300; 356/73.1; 356/141.3
(58) Field of Search ............................ 702/22, 33, 40, 702/49, 134; 250/339.02, 339.12, 341.8, 339.11, 360.1; 356/141.3–141.4, 139.04–139.08, 300, 326, 73.1

(56) References Cited

U.S. PATENT DOCUMENTS

| | | | |
|---|---|---|---|
| 3,578,866 A | 5/1971 | Kohler et al. | 356/74 |
| 3,597,616 A | 8/1971 | Brunton et al. | 250/83.3 |
| 3,776,642 A | 12/1973 | Anson et al. | 356/188 |
| 3,861,788 A | 1/1975 | Webster | 350/315 |
| 3,876,881 A | 4/1975 | Bohlen | 250/361 C |
| 3,886,331 A | 5/1975 | Schierer | 356/308 |
| 4,037,970 A | 7/1977 | Webster et al. | 356/188 |
| 4,040,747 A | 8/1977 | Webster | 356/188 |
| 4,108,847 A | 8/1978 | Creinin et al. | 260/112 G |
| 4,146,332 A | 3/1979 | Moore | 356/308 |
| 4,253,766 A | 3/1981 | Funk | 356/418 |
| 4,260,262 A | 4/1981 | Webster | 356/418 |
| 4,448,790 A | 5/1984 | Sarkki et al. | 426/52 |
| 4,463,261 A | 7/1984 | Bowman | 250/339 |
| 4,540,282 A | 9/1985 | Landa et al. | 356/328 |
| 4,560,275 A | 12/1985 | Goetz | 356/326 |

(List continued on next page.)

FOREIGN PATENT DOCUMENTS

| | | |
|---|---|---|
| EP | 0 388 082 | 9/1990 |
| WO | WO 99/40419 | 8/1999 |

OTHER PUBLICATIONS

Randy Nouis, Predicting the Ninety–Fifth Percentile Dust Environment for Passenger Vehicles in the Continental United States, Mar. 1–5, 1993, pp. 1–11.

(List continued on next page.)

*Primary Examiner*—John Barlow
*Assistant Examiner*—Hien Vo
(74) *Attorney, Agent, or Firm*—Snell & Wilmer LLP

(57) ABSTRACT

An optical sensor for use in measuring constituents of an agricultural product. An optical sensing window passes a stream of the agricultural product, and a radiation source irradiates the stream as it passes through the optical sensing window. A receiver receives radiation transmitted through the stream and converts it into a corresponding electrical signal using a spectrometer. The electrical signal is digitized to produce a series of data points corresponding to particular wavelengths. A processor normalizes the data points using a reference value in order to generate processed data points that can be used to predict a constituent content of the agricultural product.

43 Claims, 20 Drawing Sheets

U.S. PATENT DOCUMENTS

| | | | |
|---|---|---|---|
| 4,649,281 A | 3/1987 | Schmitt et al. | 250/574 |
| 4,806,764 A | 2/1989 | Satake | 250/339 |
| 4,836,017 A | 6/1989 | Bozek | 73/152.42 |
| 4,866,644 A | 9/1989 | Shenk et al. | 364/571.02 |
| 4,925,305 A | 5/1990 | Erickson | 356/300 |
| 4,997,280 A | 3/1991 | Norris | 356/308 |
| 5,130,158 A | 7/1992 | Otsubo et al. | 426/622 |
| 5,132,538 A | 7/1992 | Norris | 250/339 |
| 5,173,079 A | 12/1992 | Gerrish | 460/7 |
| 5,212,765 A | 5/1993 | Skeirik | 395/11 |
| 5,218,529 A | 6/1993 | Meyer et al. | 702/28 |
| 5,224,203 A | 6/1993 | Skeirik | 395/22 |
| 5,239,180 A | 8/1993 | Clarke | 250/339 |
| 5,241,178 A * | 8/1993 | Shields | 250/339.02 |
| 5,258,825 A * | 11/1993 | Reed et al. | 356/402 |
| 5,308,981 A | 5/1994 | Perten | 250/339.01 |
| 5,317,524 A | 5/1994 | Das et al. | 702/134 |
| 5,327,708 A | 7/1994 | Gerrish | 56/1 |
| 5,351,338 A | 9/1994 | Wigren | 704/219 |
| 5,406,084 A * | 4/1995 | Tobler et al. | 250/339.01 |
| 5,410,021 A | 4/1995 | Kampen | 530/372 |
| 5,442,438 A | 8/1995 | Batchelder et al. | 356/301 |
| 5,448,069 A | 9/1995 | Tobler et al. | 250/339.01 |
| 5,472,511 A | 12/1995 | Rayas et al. | 127/67 |
| 5,478,748 A | 12/1995 | Akins, Jr. et al. | 436/86 |
| 5,517,302 A | 5/1996 | Stearns et al. | 356/326 |
| 5,559,034 A | 9/1996 | Roberts et al. | 435/320.1 |
| 5,578,931 A | 11/1996 | Russell et al. | 324/536 |
| 5,605,577 A | 2/1997 | Rayas et al. | 127/67 |
| 5,616,851 A | 4/1997 | McMahon et al. | 73/29.01 |
| 5,617,511 A | 4/1997 | Bigus | 375/26 |
| 5,619,618 A | 4/1997 | Bigus | 395/23 |
| 5,689,333 A | 11/1997 | Batchelder et al. | 356/301 |
| 5,697,373 A | 12/1997 | Richards-Kortum et al. | 128/664 |
| 5,751,421 A | 5/1998 | Wright et al. | 356/328 |
| 5,755,672 A | 5/1998 | Arai et al. | 600/547 |
| 5,844,086 A | 12/1998 | Murray | 530/377 |
| 5,898,792 A | 4/1999 | Oste et al. | 382/110 |
| 5,986,749 A | 11/1999 | Wu et al. | 356/73.1 |
| 5,991,025 A | 11/1999 | Wright et al. | 356/328 |
| 6,001,412 A | 12/1999 | Huber et al. | 426/656 |
| 6,005,076 A | 12/1999 | Murray | 530/377 |
| 6,100,526 A | 8/2000 | Mayes | 250/339.11 |
| 6,285,198 B1 | 9/2001 | Nelson et al. | 324/664 |

OTHER PUBLICATIONS

C. S. Chang et al., Grain Flow Regulator for Dust Emission Control, Nov.–Dec., 1985, pp. 2059–2062.

Joseph A. Borgia et al., Pressure Drop and Flow Characteristics for a Heavy–Duty Air Filter During Dust Loading, Nov. 16–19, 1987, pp. 1–15.

Charles O. Reinhart et al., Measurement of Engine Air Cleaner Efficiency Using Airborne Particle Size Analysis, Sep. 12–15, 1983, pp. 1–8.

Philip C. Williams, et al.; Determination of Protein and Moisture in Wheat and Barley by Near–Infrared Transmission, 1985, pp. 239–244.

K. H. Norris et al., Optimization of Mathematical Treatments of Raw Near–Infrared Signal in the Measurement of Protein in Hard Red Spring Wheat. I. Influence of Particle Size, 1984, pp. 158–165.

Renfu Lu et al., Determination of Firmness and Sugar Content of Apples Using Near–Infrared Diffuse Reflectance, 24 pages.

F. De Lene Mirouze et al., Quantitative Analysis of Glucose Syrups by ATR/FT–IR Spectroscopy, 1993, pp. 1187–1191.

Véronique Bellon–Maurel et al., Quantitative Analysis of Individual Sugars during Starch Hydrolysis by FT–IR/ATR Spectrometry. Part I: Multivariate Calibration Study—Repeatibility and Reproducibility, 1995, pp 556–562.

Suranjan Panigrahi, et al., On–The–Go Sensing Techniques for Sugar Determination of Sugarbeet in the Field, pp 176–178.

E. K. Kemsley et al., Quantitative analysis of sugar solutions using infrared spectroscopy, 1992, pp299–304.

Dr. Daniel S. Humburg et al., Spectral Analysis of Sugar Beet Canopy for Spatial and Temporal Quantification of Sugar Content, Quality, and Disease, Dec. 14, 1999, pp. 1–6.

Dave Berard, Protein Monitor on the Market, 07/97, pp. 18–19.

Carol R. Dumas, New Milestone Monitor Analyzes Grain Quality On The Go, Feb. 14, 1997, pp. 1–4.

Jerry Workman, Jr., A Compact Reference for Practitioners, pp. Contents and 423–435.

Food Processing Automation, May 6, 1990, pp. Table of Contents and 103–114.

Donald A. Burns, Handbook of Near–Infrared Analysis, pp. Contents 53–106.

P. C. Williams et al., Effect of Mutual Interactions on the Estimation of Protein and Moisture in Wheat, Nov. 24, 1982.

Russell Tkachuk, Ph.D., Protein Analysis of Whole Wheat Kernels by Near Infrared Reflectance [1,2].

G. Downey et al., Protein Testing of Wheat by Near Infrared Reflectance.

Frédéric Cadet et al., Direct Spectroscopic Sucrose Determination of Raw Sugar Cane Juices, 1997, pp 166–171.

Gianluigi Marchetti, Application of a NIR on–line automatic analyzer system in a beet sugar factory, 1990, pp 210–215.

Nils Berding et al., Crop Ecology, Production & Management, 1991, pp 1017–1023.

Nils Berding et al.; Near Infrared Reflectance Spectroscopy for Analysis of Sugarcane from Clonal Evaluation Trials: II. Expressed Juice, 1991, pp 1024–1028.

Roberto Giangiacomo et al., Near Infrared Spectrophotometric Determination of Individual Sugars in Aqueous Mixtures, 1986, pp 679–683.

Stephen R. Delwiche et al., Classification of Hard Red Wheat by Near–Infrared Diffuse Reflectance Spectroscopy, 1993, pp. 29–35.

Huaipu Song et al., Neural Network Classification of Wheat Using Single Kernel Near–Infrared Transmittance Spectra, Oct. 1995, pp. 2927–2934.

Stephen R. Delwiche, Single Wheat Kernel Analysis by Near–Infrared Transmittance: Protein Content, 1995, pp. 11–16.

Philip C. Williams, Application of Near Infrared Reflectance Spectroscopy to Analysis of Cereal Grains and Oilseeds, 1975, pp. 561–576.

Near–Infrared Reflectance Method for Protein Determination, pp. 1–2.

Near–Infrared Method for Protein Content in Whole–Grain Wheat, pp. 1–3.

Innovative Protein Monitoring, pp. 1–2.

File History—U.S. Appl. No. 5,751,421.

J. Sorvaniemi et al., Using Partial Least Squares Regression and Multiplicative Scatter Correction of FT–NIR Data Evaluation of Wheat Flours, 1993, pp 251–258.

Suming Chen et al., "Neural Network Analysis of Sugar Content in Fruit Juice", Jul. 18–21, 1999, pp. Title page thru 12.

Renfu Lu et al., "Determination of Sugar Content and Firmness of Apples Using Near–Infrared Diffuse Reflectance", 07/9–12, 00, pp. Title page thru 16.

K. J. Kaffka et al., "Attempts to Determine Oil, Protein, Water and Fiber Content in Sunflower Seeds by the NIR Technique", 1983, pp 117–129.

Essex E. Finney, Jr. et al., "Determination of Moisture in Corn Kernals by Near–Infrared Transmittance Measurements", 1978, pp 581–584.

Wang–Sheng Li et al., "Determination of Rough Rice Quality by a Portable Near–Infrared Spectroscopy", 1997, (5) pages.

D. T. Lamb et al., "Moisture Determination in Single Soybean Seeds by Near–Infrared Transmittance", 1991, pp 2123–2129.

P. C. Williams et al., "Influence of Temperature on Estimation of Protein and Moisture in Wheat by Near–Infrared Reflectance", 1982, pp473–477.

D. Wang et al., "Effect of Wheat Kernel Size and Orientation on Reflectance Spectra and Single Kernel Color Classification", 1997, pp 1–34.

S. R. Delwiche, "Measurement of Single–Kernel Wheat Hardness Using Near–Infrared Transmittance", 1993, pp1431–1437.

M. R. Campbell et al., "Whole Grain Amylose Analysis in Maize Using Near–Infrared Transmittance Spectroscopy", 1997, pp300–303.

Stermer et al., "Infrared Reflectance Spectroscopy for Estimation of Moisture of Whole Grain", 1997, pp345–351.

F. E. Dowell et al., "Automated Single Wheat Kernel Quality Measurement Using Near–Infrared Reflectance", 1997, pp 1,3,5,7 and 9.

B. G. Osborne, "Recent Progress in the Application of NIR to the Measurement of Quality Parameters in Flour", 1982, pp577–581.

J. S. Shenk, "How NIR Can Help in Measuring Forage Quality for Breeding and Utilization Programs", (3) pages.

Gerard Downey, "Estimation of Moisture in Undried Wheat and Barley by Near Reflectance", 1985, pp951–958.

Doninique Bertrand et al., "Application of Principal Component Analysis to the Prediction of Lucerne Forage Protein Content and in vitro Dry Matter Digestibility by NIR Spectroscopy", 1987, pp299–307.

Shuso Kawamura et al., "Determining Undried Rough Rice Constituent Content Using Near–Infrared Transmission Spectroscopy", 1997, pp cover, 1,3,5 and 7.

Holger M. Jaenisch et al., "Instrumentation to Measure the Near–IR Spectrum of Small Fruits", 1990, pp 162–166.

Paul Geladi et al., "Partial Least–Squares Regression: A Tutoria", 1985, pp 1–17.

Constantinos Goutis, "Second–Derivative Functional Regression with Applications to Near Infra–Red Spectroscopy", 1998, pp 103–114.

Milling Feed and Fertiliser, "FMBRA takes the Grind out of Measuring Moisture", pp 34–35.

John S. Shenk et al., "Near Infrared Reflectance Analysis with Single–and Multiproduct Calibrations", 1993, pp582–584.

D. T. Williams et al., "The Derivative Spectrometer", 1970, pp 1597–1605.

F. E. Barton et al., "The Calibration of NIR Reflectance Spectrometer for the Determination of Diverse Compositional Parameters", 1988, pp 768–773.

R. J. Barnes et al.; "Standard Normal Variate Transformation and De–Trending of Near–Infrared Diffuse Reflectance Spectra", 1989, pp772–777.

Kurt C. Lawrence et al., "Sensing Wheat Moisture Content Independent of Density", 1997, pp Cover Page, 1,3,5,7,9, 11,13 and 15.

Abraham Savitzky et al., "Smoothing and Differentiation of Data by Simplified Least Squares Procedures", 1964, pp1627–1639.

Principle Introduction to PROTRONICS, (8) pages.

"Comments on the Savitzky–Golay Convolution Method for Least–Squares Fit Smoothing and Differentiation of Digital Data", 1978, pp1383–1386.

Gerald S. Birth et al., "Interaction Between Light and Natural Materials: Laboratory Demonstrations", (4) Cover Pages, and pp1–36.

Gerald S. Birth, "How Light Interacts with Foods", (6) pages.

H. Martens et al., "Partial Least Squares Regression: A New Two–Stage NIR Calibration Method", 1982, pp607–647.

Tormod Næs et al., "Comparison of Multivariate Calibration and Discriminant Analysis in Evaluating NIR Spectroscopy for Determination of Meat Tenderness", 1996, pp350–357.

G. Asimopoulos et al., "On–Line Monitoring of Dairy Products with the Use of NIR Technology", pp 266–271.

"Comments on Smoothing and Differentiation of Data by Simplified Least Square Procedure", 1972, pp 1906–1910.

Edward K. Baldwin, Ph.D., "Calibrating Near Infrared Instruments for On–Line Food Processing Measurements", pp 252–265.

P. D. Wilson et al., "Polynomial Filters of any Degree", 1981, pp 599–603.

L. P. McDermott, "The Benefits and Pitfalls of Applying Near Infrared Analysis On–Line", pp 103–114.

B. G. Osborne, "Monitoring the accuracy of NIR Instruments", 1987, pp 515–521.

James R. Long, "Spectroscopic Calibration and Quantitation Using Artificial Neural Networks", 1990, pp 1791–1797.

Phil Williams et al., "Near–Infrared Technology in the Agricultural and Food Industries", (18) pages.

B. G. Osborne et al., "Practical NIR Spectroscopy with Application in Food and Beverage Analysis", (16) pages.

Jerry Workman, Jr. et al., "Applied Spectroscopy A Compact Reference for Practitioners", (10) pages.

Reginald H. Wilson, "Spectroscopic Techniques for Food Analysis", (9) pages.

Kerstin Jakobsson, Foss Tecator AB, "Reliable Grain Trading Based on Professional Decisions", 1998 (4) pages.

* cited by examiner

OPTICAL SENSOR FOR ANALYZING A STREAM OF AN AGRICULTURAL PRODUCT TO DETERMINE ITS CONSTITUENTS

REFERENCE TO RELATED APPLICATIONS

The present application is a continuation-in-part of U.S. provisional patent application Ser. No. 60/164,161, filed Nov. 8, 1999, and entitled "Optical Analysis of Grain Stream," which is incorporated herein by reference.

The present application is related to the following application, which is incorporated herein by reference: U.S. provisional patent application Ser. No. 60/175,636, filed Jan. 12, 2000, and entitled "On-The-Go Sugar Sensor for Determining Sugar Content During Harvesting."

FIELD OF THE INVENTION

The present invention relates to a method and apparatus for optically analyzing a stream of an agricultural product in order to determine constituents of the product.

BACKGROUND OF THE INVENTION

Systems are known in the art for the optical analysis of a stream of grain. As the grain is harvested in the field, a light source passes light through the grain stream. The transmitted light is detected by a receiver and processed by a computer under software control. By comparing the spectral absorption with values representing known absorption, the grain can be analyzed to determine its constituents. Examples of systems for handling grain are disclosed in U.S. Pat. Nos. 5,343,761 and 5,369,603, both of which are incorporated herein by reference.

To make that determination, a reference value is used. For example, the light can be transmitted to a white ceramic tile without grain present. The light reflected and received from the tile provides a reference value for use in analyzing the light as reflected from the grain. The use of a tile can have disadvantages. It can become dusty, particularly from the grain, and the dust can affect the light reflected from the tile. Therefore, the dust can alter the reference value and affect the accuracy of the analysis. In addition, the use of a tile to obtain a reference value only works for analyzing a signal reflected from the grain, since the reference is obtained from a reflected signal. Other references must be used for analyzing a signal transmitted through the grain.

Accordingly, a need exists for improvements in these systems for optical analysis of agricultural products.

SUMMARY OF THE INVENTION

An apparatus consistent with the present invention is used for measuring a constituent content of an agricultural product. It includes a device for forming a stream of the agricultural product, and an optical sensing window for passing the stream of the agricultural product. A radiation source irradiates the stream of the agricultural product as it passes through the optical sensing window, and a receiver receives radiation transmitted through the stream and converts it into a corresponding electrical signal. A computer receives the electrical signal and processes it in order to generate data for use in determining a constituent content of the agricultural product.

A method consistent with the present invention converts a light signal into an electrical signal for use in predicting a constituent content of an agricultural product. It includes receiving a light signal from an agricultural product and converting the light signal into an electrical signal. The electrical signal is digitized to produce a plurality of data points, which are then normalized using a reference signal value to produce a plurality of normalized data points. The reference signal value corresponds with a magnitude at a wavelength of the light signal substantially unaffected by the constituent content. The normalized data points have information related to a constituent content of the agricultural product and can thus be used to predict the constituent content.

BRIEF DESCRIPTION OF THE DRAWINGS

The accompanying drawings are incorporated in and constitute a part of this specification and, together with the description, explain the advantages and principles of the invention. In the drawings.

DETAILED DESCRIPTION

Overview

Figure 1:
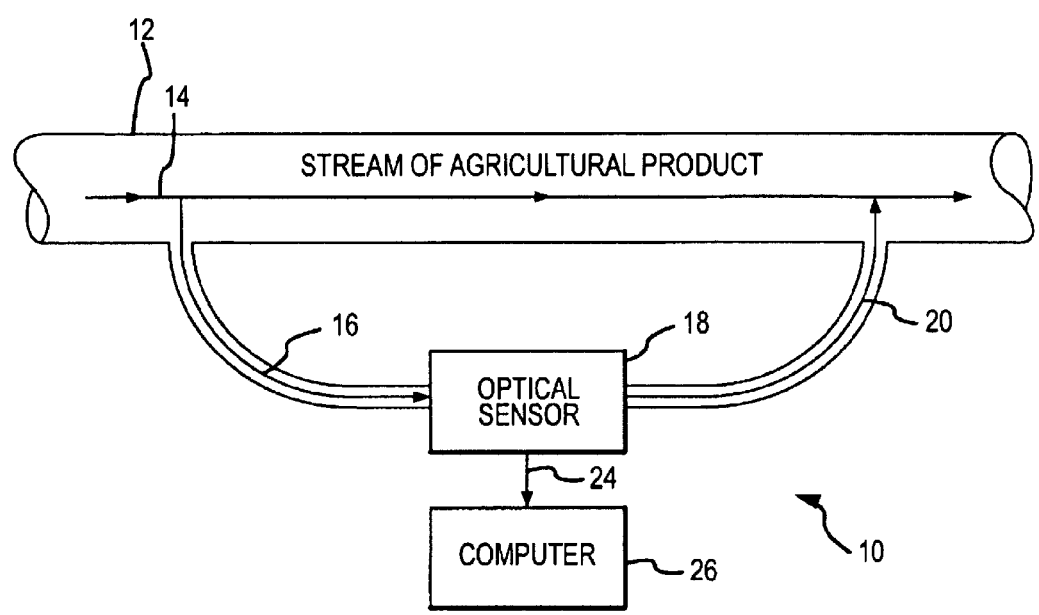
FIG. 1 is a diagram illustrating optical analysis of a stream of agricultural products consistent with the present invention.

FIG. 1 illustrates a system 10 for optical analysis of a stream of an agricultural product consistent with the present invention. In system 10, a stream of an agricultural product 14 is produced within a conduit 12. From the stream of agricultural product 14 a portion of it 16 is directed to an optical sensor 18. Following analysis of portion 16, it is returned as portion 20 to the stream of agricultural product 14 within conduit 12. Accordingly, optical sensor 18 analyzes a portion of a stream of an agricultural product from a conduit of the product and then returns that portion, or most of it, back to the stream of the agricultural product.

The stream of agricultural product 14 and conduit 12 can be derived from a variety of sources. For example, conduit 12 may represent a pipe within a combine as it harvests a field of an agricultural product such as grain. In addition, conduit 12 may alternatively represent a pipe transporting grain within a food processing facility. Therefore, optical sensor 18 provides an advantage of operating on a stream of grain at various locations, such as in the field or within an assembly line of a food processing plant, and provides in real-time or near real-time an indication of a constituent content of the stream of agricultural product.

Optical system 18 analyzes portion 16 of the agricultural product using optical sensing components. As further explained below, optical sensor 18 transmits light through the stream of the agricultural product and receives light from the agricultural product, either transmitted through or reflected from it. The received light signal is converted to an electrical signal and transmitted on line 24 to a computer 26. The term "light signal" is intended to include visible light signals, invisible light signals, or both. Also, the term "received light signal" includes a light signal reflected from or transmitted through an agricultural product. Computer 26 digitizes the electrical signal to produce data points, and processes the data points to provide an indication of a constituent content based upon the signal and upon how various constituents affect the light absorption properties of the agricultural product. Once the constituent content is predicted, computer 26 may store and output an indication of that constituent content in a variety of forms. During the operation, because of random size configurations of grain samples and the intra-granular space, the transmitted light through the product could saturate the receiver. In that case, computer 26 can be programmed to detect this event and change the data acquisition parameter, such as integration time, of the spectrometer to acquire the raw spectral signal. Alternatively, on detecting this event, computer 26 can be programmed to trigger a motor 48 to advance the grain or agricultural product in the sensing window for a very small amount of time. This will change the configuration of the sample (product) in the sensing window, and the new configuration might not saturate the receiver.

Optical sensor 18 can be used to analyze various types of agricultural products, such as grain or wheat. Also, optical sensor 18 along with computer 26 can provide for prediction of a variety of constituents such as protein, starch, fiber, or moisture content. Also, multiple constituents can be determined through analysis of the same signal from optical sensor 18; this feature eliminates, for example, the need for separate sensors, although different sensors can still be used if desired.

Figure 2A:
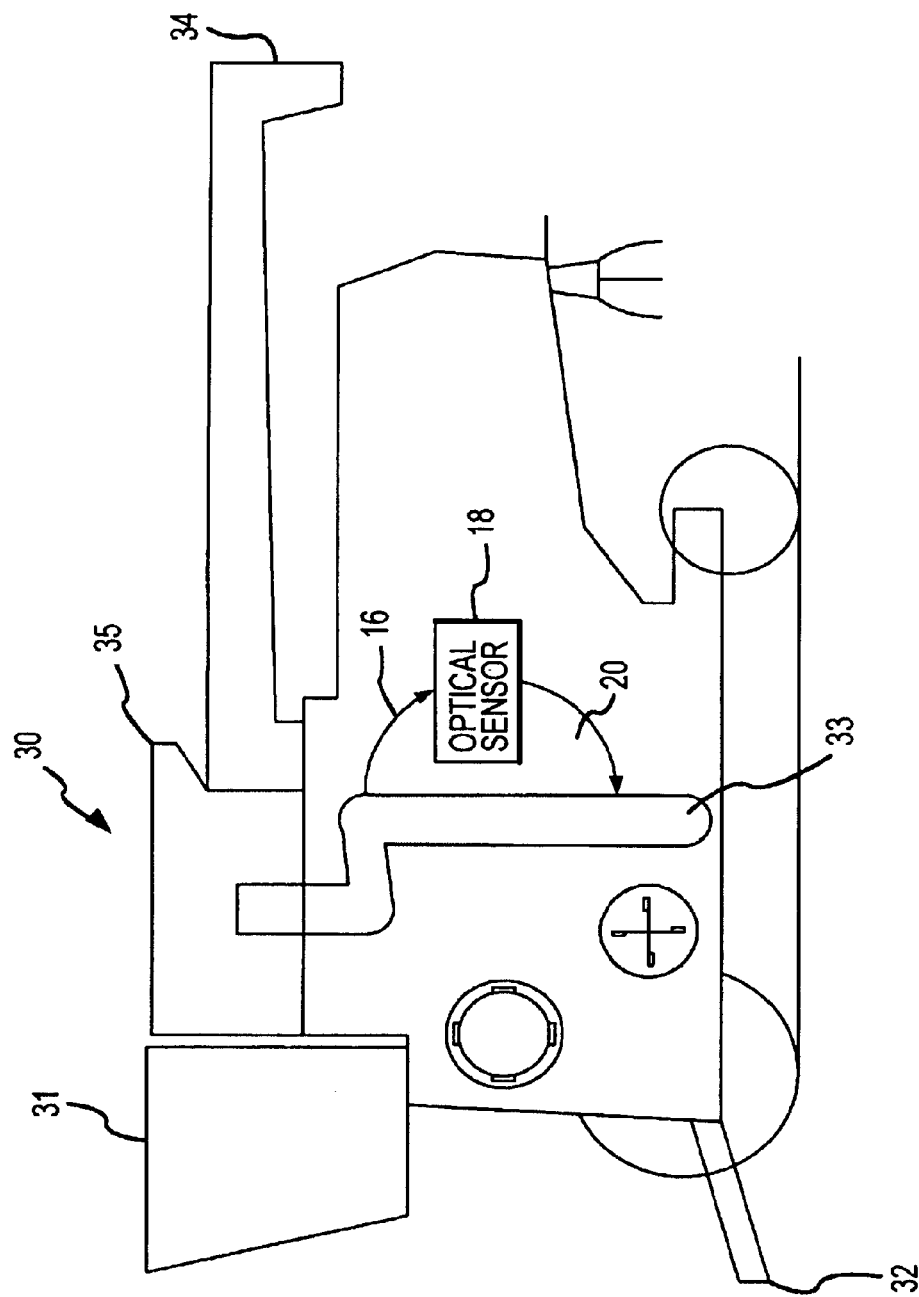
FIGS. 2A and 2B are side and rear views of a conventional combine, illustrating use of an optical sensor for analysis of a stream of an agricultural product on the combine during harvesting of the product.
Figure 2B:
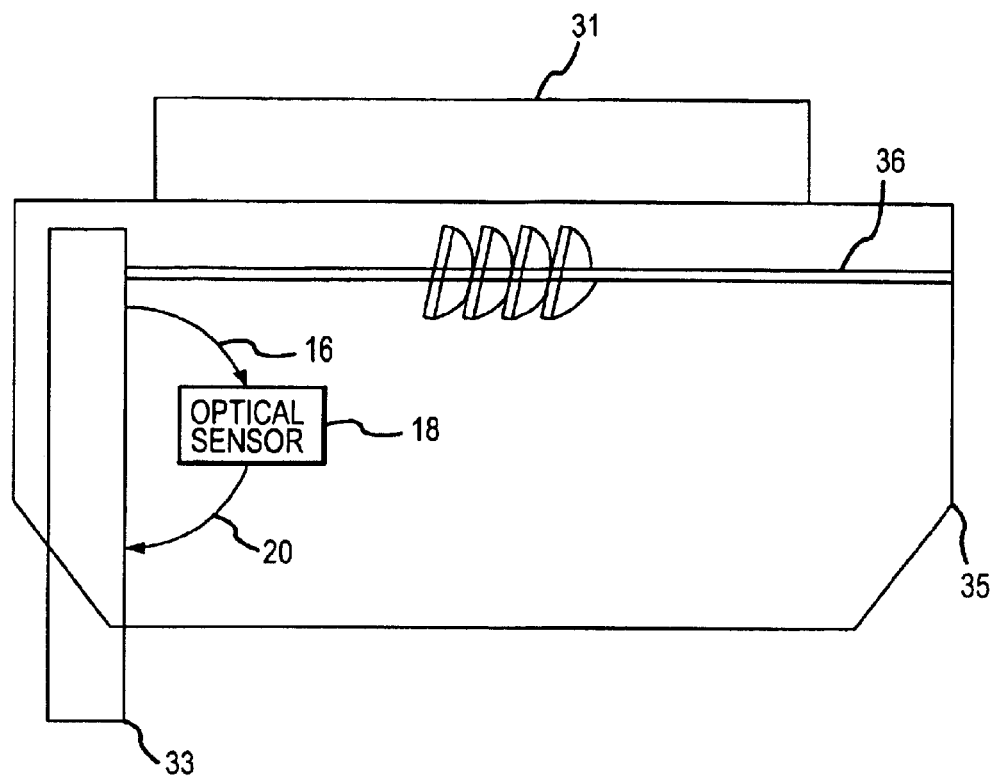

FIG. 2A illustrates use of optical sensor 18 attached to a conventional combine 30 for determining constituent contents of an agricultural product during harvesting. Conventional combine 30 includes a cab 31 for a driver to operate the combine. A combine header attachment 32 is used for attaching various devices to harvest the agricultural product. A clean grain elevator 33 can generate a stream of the agricultural product, and optical sensor 18 can thus remove a portion (16) of the stream, sample it, and return it (20) to clean grain elevator 33. A grain tank 35 holds the harvested agricultural product, and the product can be discharged through unloading auger 34 via an auger 36. As illustrated, optical sensor 18 in this example can be attached to a side of the combine (FIG. 2A) or a rear of the combine (FIG. 2B).

Optical Sensor System

Figure 3:
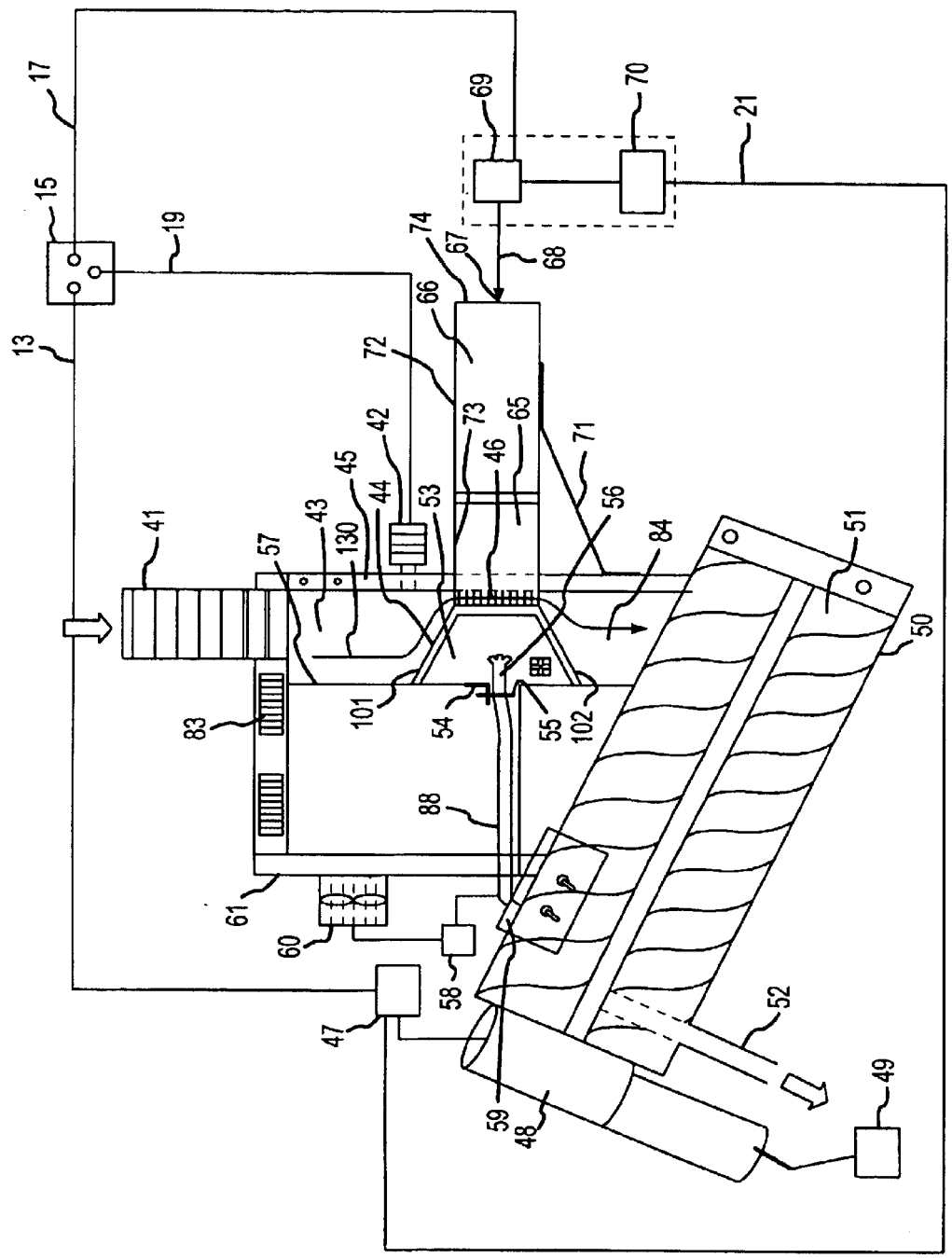
FIG. 3 is a block diagram of a system including an optical sensor for analyzing a stream of an agricultural product.
Figure 4:
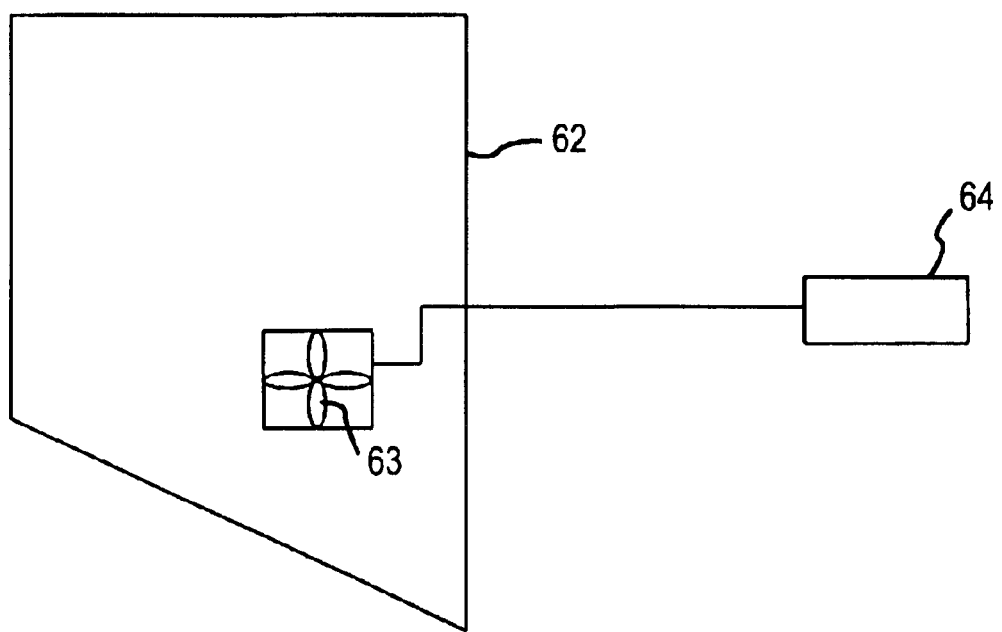
FIG. 4 is a diagram of a side cover in the system of FIG. 3.

A system to predict the protein or other constituent contents of agricultural products is illustrated with reference to FIGS. 3–9. As shown in FIG. 3, an inlet 41 of a material handling system typically includes particular pipes and accessories to connect with a source of an agricultural product depending upon a particular application and the requirements necessary to branch off a stream of the agricultural product for analysis. For example, inlet 41 can be attached to an auger, a clean grain elevator, or any outlet of a storage bin, and the term "inlet" includes any mechanism for assisting in forming a stream of an agricultural product for analysis. The grain or agricultural product entering through inlet 41 moves through a grain passage 43, bounded by an inner transparent wall 44 and a metallic outer wall 45. The grain entering through inlet 41 passes through an optical sensing window 46, as illustrated by arrow 130.

A proximity sensor 42 is connected to a control unit 47, which is also connected to an electric motor 48 operated by direct current (DC) power source 49. Electric motor 48 is mounted within an enclosure box of an auger 50 containing discharger auger 51, which is driven by motor 48. Auger 51 through an outlet 52 can discharge the grain from the system back to the original stream of grain or any other user-defined location.

An illumination chamber 53 is bounded by transparent wall 44 and a vertical opaque wall 57. A base 54 is mounted on wall 57. An illumination source 56, implemented with a lamp or other device providing a light signal, is attached by a lamp holder 55 and is connected to the power source and control box 59 through a cable 88. Lamp 56 may be implemented with, for example, a tungsten-halogen lamp.

A sensor body 61 includes air inlet passages 83. Sensor body 61 is attached to a DC fan 60. A side cover 62 of sensor body 61 (shown in FIG. 4) has another fan 63 mounted on the cover and is operated by a DC power source 64.

A sensor head 72 is composed of optical passage 65, optically isolated from outer environment by metallic covers 73 and a detector box 66. Sensor head 72 is attached to sensor body 61 by a mount 71. The tip of a fiber optic probe 67 is mounted on detector wall 74 (see FIG. 5) of detector box 66. Fiber optic cable 68 is connected to a portable spectrometer 69 including a diffraction grating and an array of charged coupled device (CCD) detectors. Spectrometer 69 is coupled to with a computer 70. Detector box 66 and spectrometer 69 together form a receiver for converting the light signal or received radiation into a corresponding electrical signal.

Figure 5:
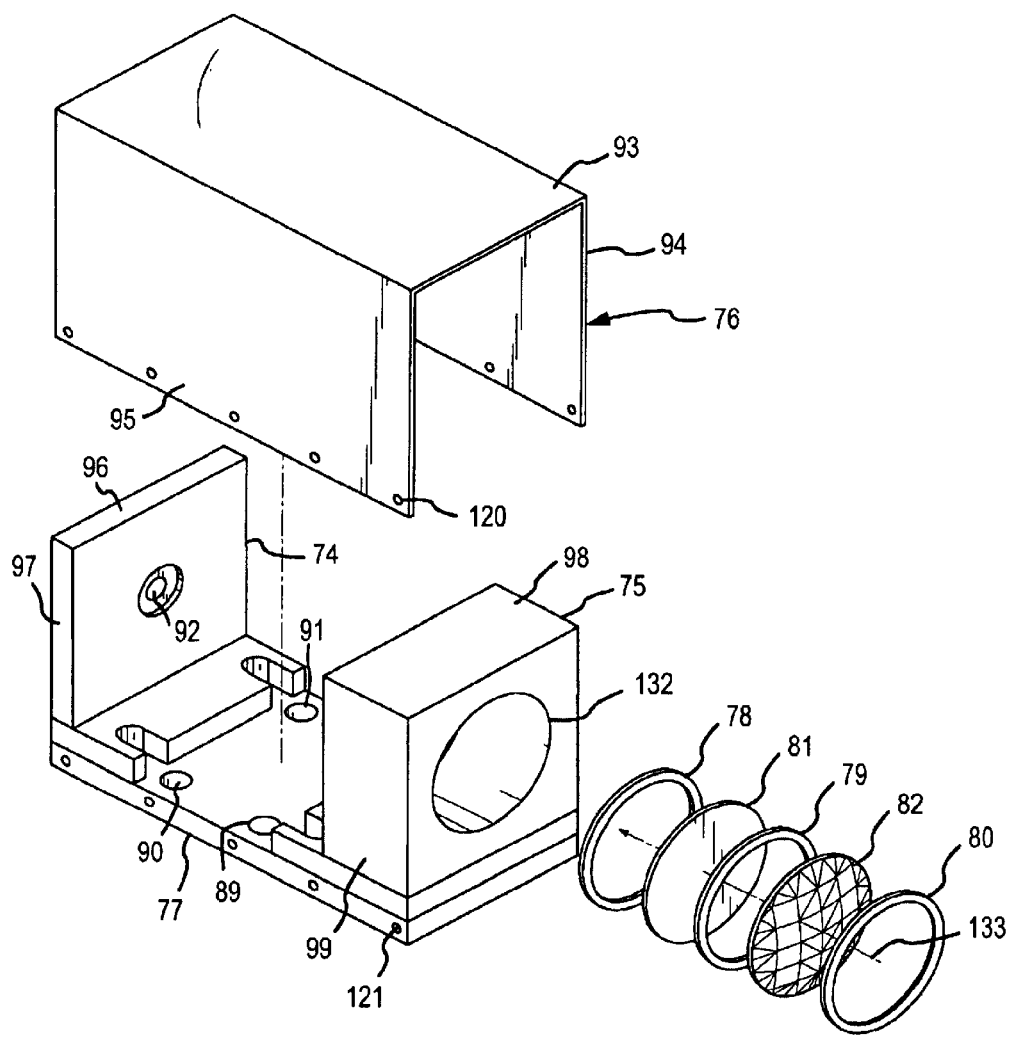
FIG. 5 is a perspective diagram of a detector box in the system of FIG. 3.

As shown in FIG. 5, detector box 66 is composed of a front lens wall 75, a detector wall 74, a base plate 77, and a top cover 76. Front lens wall 75 contains two lenses, 81 and 82 (in series) arranged between three retainers 78, 79, and 80. Cover 76 includes a top 93, and sides 94 and 95. In use, cover 76 may be fastened to base plate 77 by inserting fasteners through apertures on sides 94 and 95 such as aperture 120. The fasteners may then engage corresponding apertures on the bottom of base plate 77, such as aperture 121, for receiving a fastener through aperture 120. As shown, the bottom portions of sides 94 and 95 include a plurality of such apertures for receiving a plurality of fasteners for attachment to base plate 77.

Also, base plate 77 includes a plurality of apertures such as apertures 89, 90 and 91 for receiving fasteners and attaching base plate 77 to a bracket 71 (see FIG. 3). Although bracket 71 is shown as angled in the side view of FIG. 3, it can also be implemented with a perpendicular bracket or other configurations of brackets to support detector box 66 in this embodiment. When cover 76 is mounted on base plate 77, top 93 is set flush against top portions 96 and 98, and sides 94 and 95 are set flush against sides portion 74, 75, 97, and 99. Therefore, cover 76 provides for blocking of ambient light within detector box 66.

Detector wall 74 includes an aperture 92 for receiving and mounting an end of fiber optic cable at point 67. In addition, front lens wall 75 includes an aperture 132 for receiving the lens for focusing the received light, as illustrated by line 133, on an end of the fiber optic cable in aperture 92.

Optical Sensing Window

Figure 6:
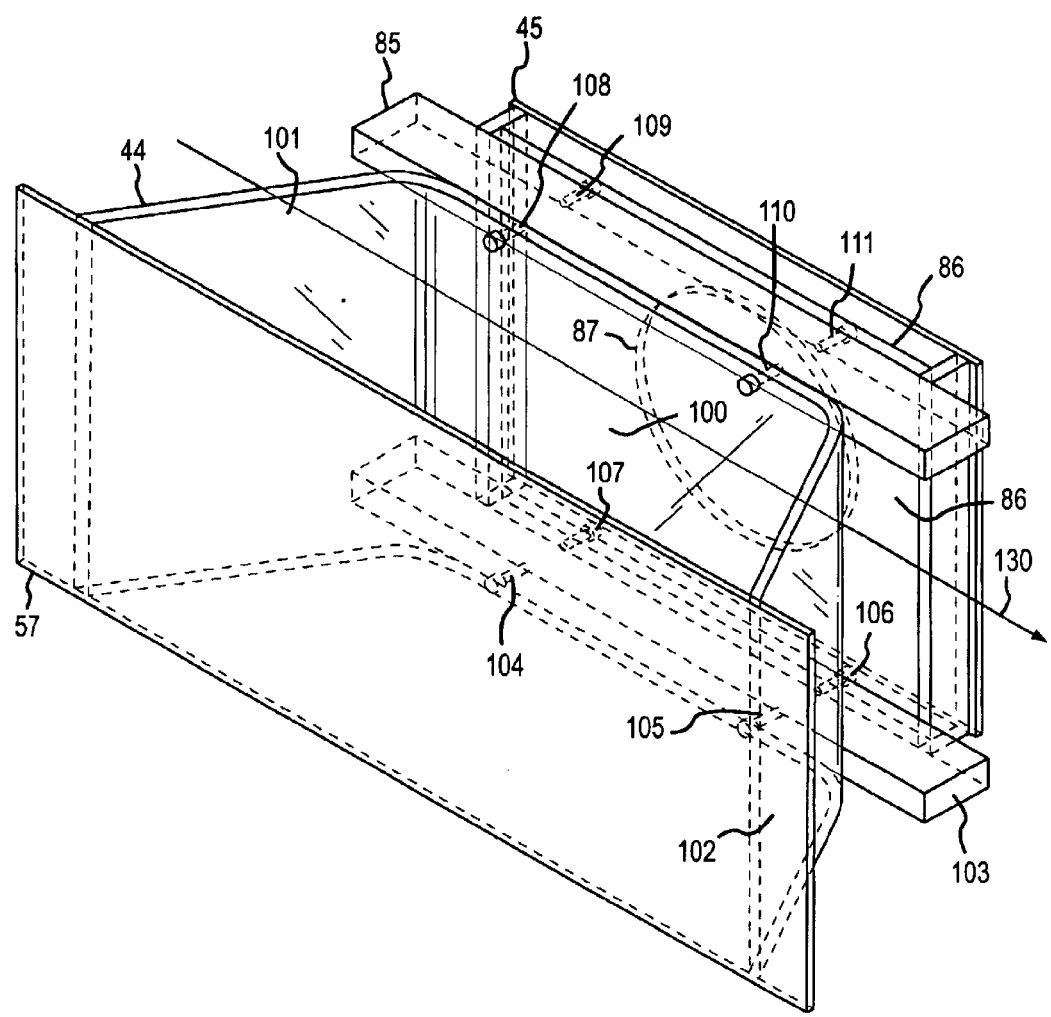
FIG. 6 is a perspective view of an optical sensing window in the system of FIG. 3.
Figure 7:
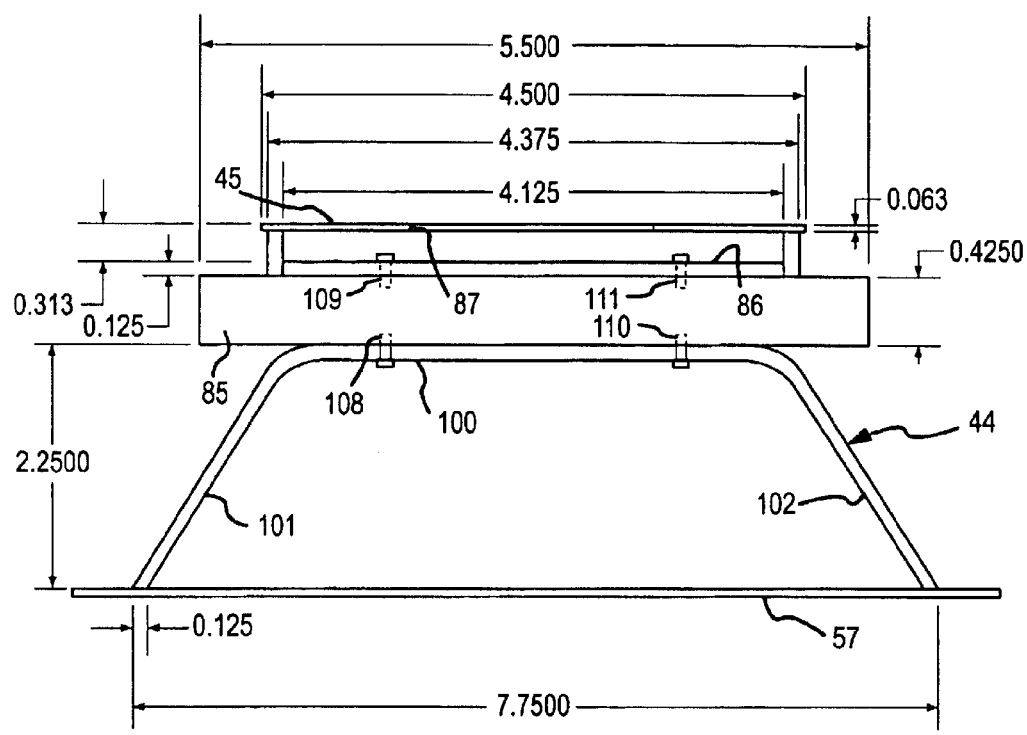
FIG. 7 is a side view of the optical sensing window.
Figure 8:
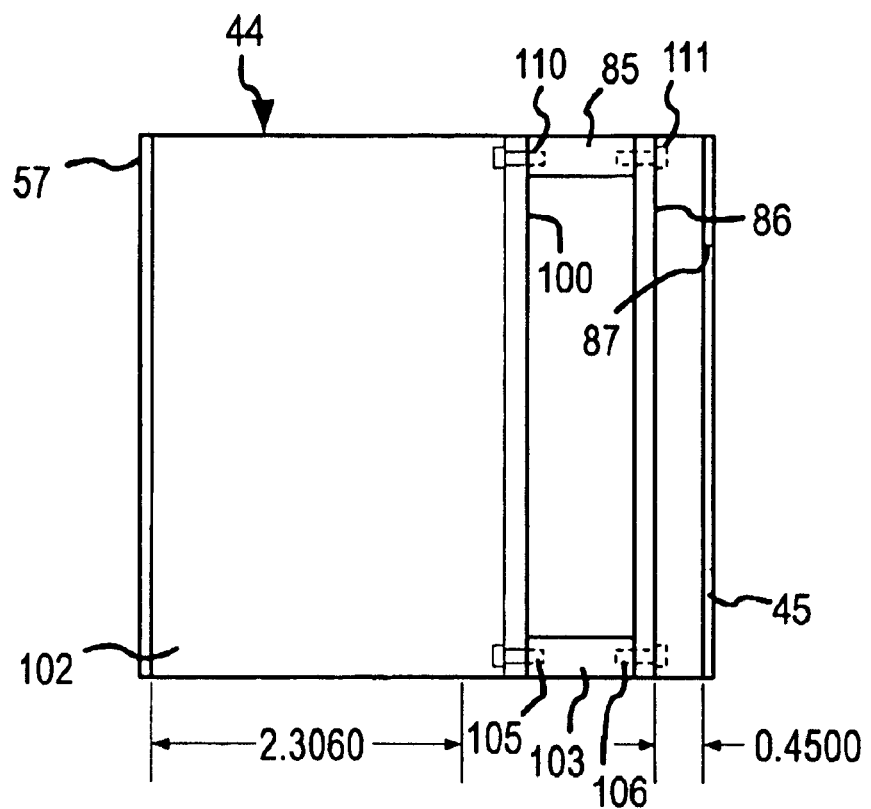
FIG. 8 is a top view of the optical sensing window.
Figure 9:
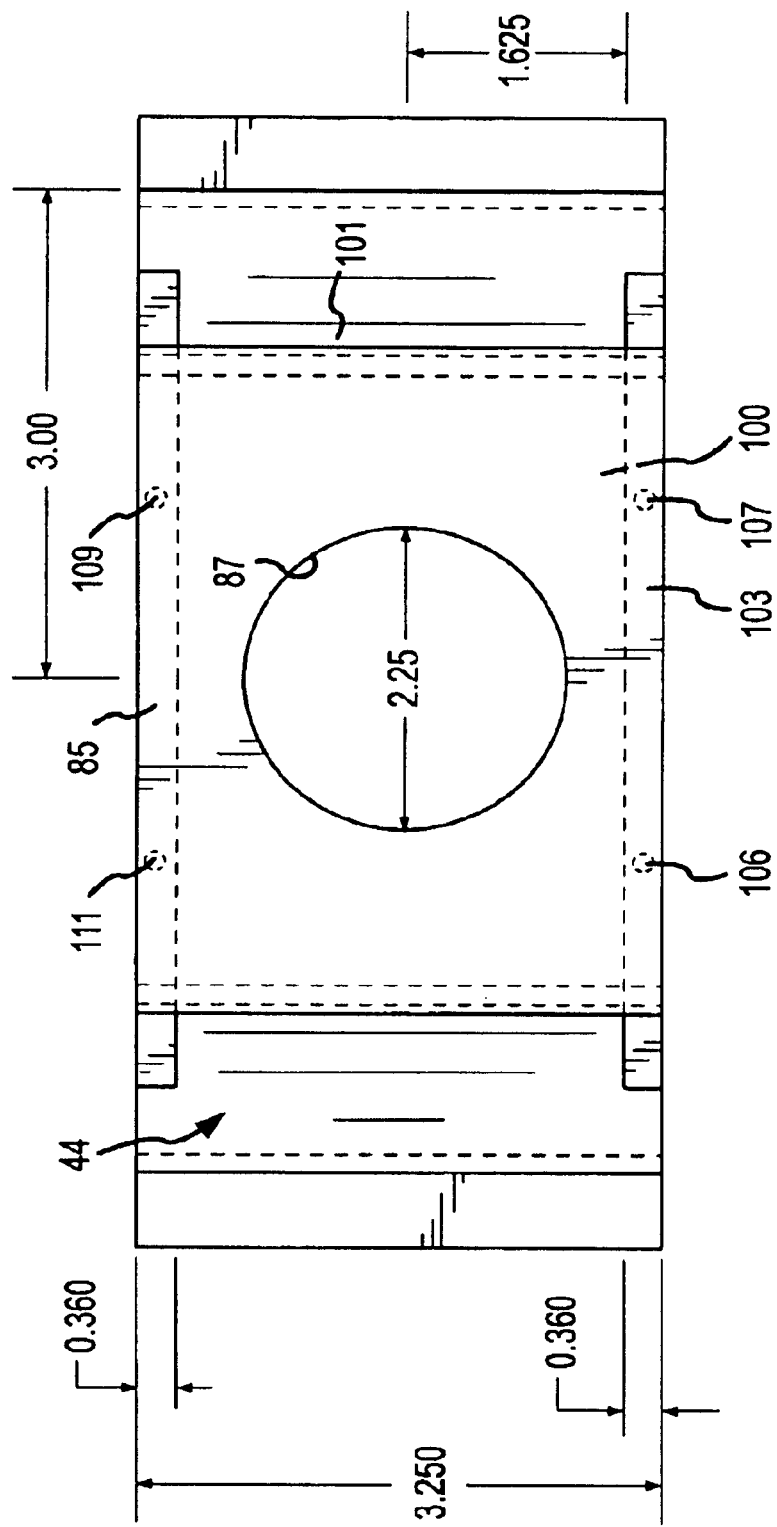
FIG. 9 is a front view of the optical sensing window.

FIG. 6 is a perspective view providing more detail of optical sensing window 46 in the system of FIG. 3. FIGS. 7–9 are, respectively, side, top, and front views also providing more detail of optical sensing window 46. The dimensions provided in FIGS. 7–9 are in inches and illustrate a preferred dimensional configuration for optical sensing window 46. An optical sensing window includes any device for providing a way to pass a light signal through a stream of an agricultural product, and optical sensing window 46 is one such example. Also, optical sensing windows can be configured according to different dimensions than those illustrated.

As shown in FIGS. 6–9, optical sensing window 46 is formed by inner transparent wall 44, and outer sensing wall 86, located behind metallic outer wall 45. The two side walls 85 and 103 of the optical sensing window are composed of opaque materials, and they connect the inner and outer walls 44 and 86. Grain passage 43 is empty space formed by the inner transparent wall 44, outer sensing wall 86, and two side walls 85 and 103. A circular area 87 on the metallic outer wall 45 defines the effective sensing region through which the transmitted beam passes to the sensor head.

An inner transparent wall 44 includes a front planar section 100 and the angled sides 101 and 102. A plurality of fasteners 104, 105, 106, and 107 are used for fastening together a first portion of the window. Another plurality of fasteners 108, 109, 110 and 111 are used for fastening together a second portion of the window.

The stream of agricultural product passes through the window as shown by arrow 130. The structure of the optical sensing window provides for a narrower passageway for the stream of agricultural product compared with inlet 41. The narrower passageway provides for a more uniform consistency in the stream of agricultural product and provides for movement of the agricultural product that helps to prevent accumulation of dust or agricultural product on the sensing region formed by circular area 87. The narrower passageway also provides for a suitable thickness of the stream of agricultural product allowing it to produce an optimum transmission of light through the product. These features provide for more consistent and accurate readings of the light signal from the agricultural product

Optical Sensor Operation

The grain or agricultural product enters through inlet 41, and it fills up grain passage 43 and 84 and the empty space in the auger. When the level of grain reaches the level at which position or proximity sensor 42 is located, the sensor outputs a signal. A switch 15 selectively connects proximity sensor 42 either to control unit 47 via line 19 connected to line 13, or to spectrometer 69 via line 19 connected to line 17. When proximity sensor 42 is connected to control unit 47, it triggers, via the signal detecting the level of grain at the sensor control, unit 47 to turn on motor 48 and run auger 51. The running of the auger allows the grain to move through auger 51 and out from the system through outlet 52. The location of position sensor 42 along with features of wall 44, optical sensing window 46, grain passage 43 and 84, and auger 51, allow the grain to move at a constant rate for sampling the stream of agricultural product. This feature may also help to eliminate dust build-up on the inner wall of optical sensing window 46. Dust build-up can adversely affect performance of the sensor.

Alternatively, when proximity sensor 42 is connected to spectrometer 69, the signal from proximity sensor 42 can be transmitted from spectrometer 69 to computer 70 for use by the computer in controlling motor 48 via line 21. The signal from proximity sensor 42 indicates that the stream of agricultural product has reached a level of the sensor and is thus present in sensing window 46. Upon receiving that signal, computer 70 can turn off motor 48 via line 21 in order to stop the flow of agricultural product and sample the stopped flow. After sampling, computer 70 can signal control unit 47 to turn on motor 48 and restart the stream of agricultural product.

Accordingly, the system can sample a moving stream of agricultural product in a continuous mode or sample a stopped stream in a stop-and-go mode. Instead of controlling the motor to stop the stream, the system can alternatively use a gating mechanism in grain passage 43 to momentarily stop the flow. The mode can be determined through the position of switch 15. Switch 15 can be implemented, for example, with a mechanical switch manually controlled by a user, or with an electromechanical switch connected to computer 70 and controlled by a command signal from computer 70.

For the sampling, illumination source 56 transmits a beam containing visible and near infrared (NIR) spectrum through the flowing or stopped agricultural product in the optical sensing window 46. The transmitted light passes through optical passage 65 and subsequently passes through detector box 66. The front wall of optical system 75 of detector box 66 converges the transmitted light or radiation on the tip of fiber optic probe 67. The transmitted light/radiation is conveyed through fiber optic cable 68 to spectrometer 69. Spectrometer 69 with the use of the computer 70, under software control, records the spectral signature of the transmitted light or radiation between 700–1100 nanometers (nm) in this example for determining protein content. Other spectral ranges may be used depending on the agricultural product and constituent to be analyzed.

Computer Hardware and Related Components

Figure 10:
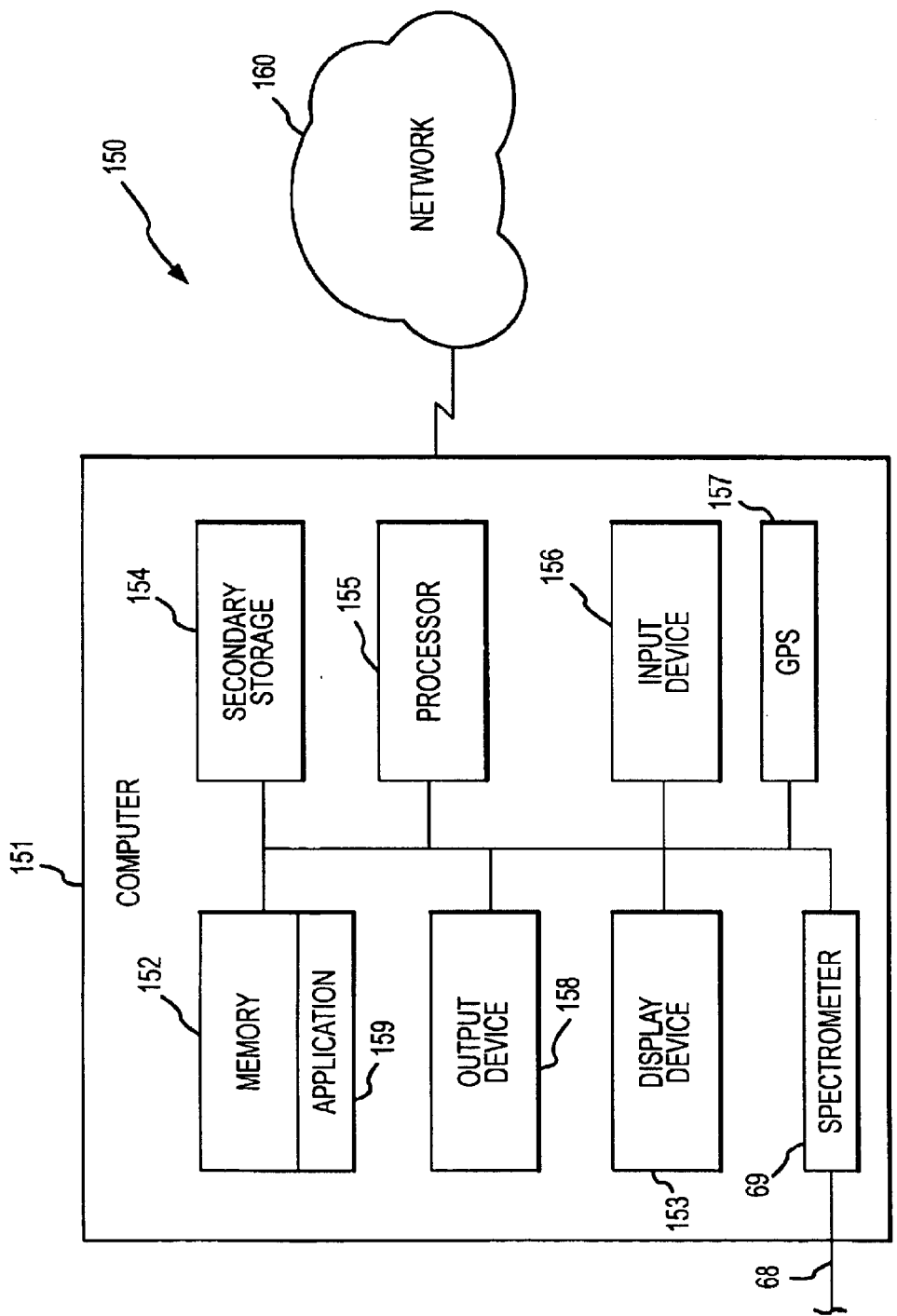
FIG. 10 is a diagram of exemplary components of a computer for use with the optical sensor.
Figure 11:
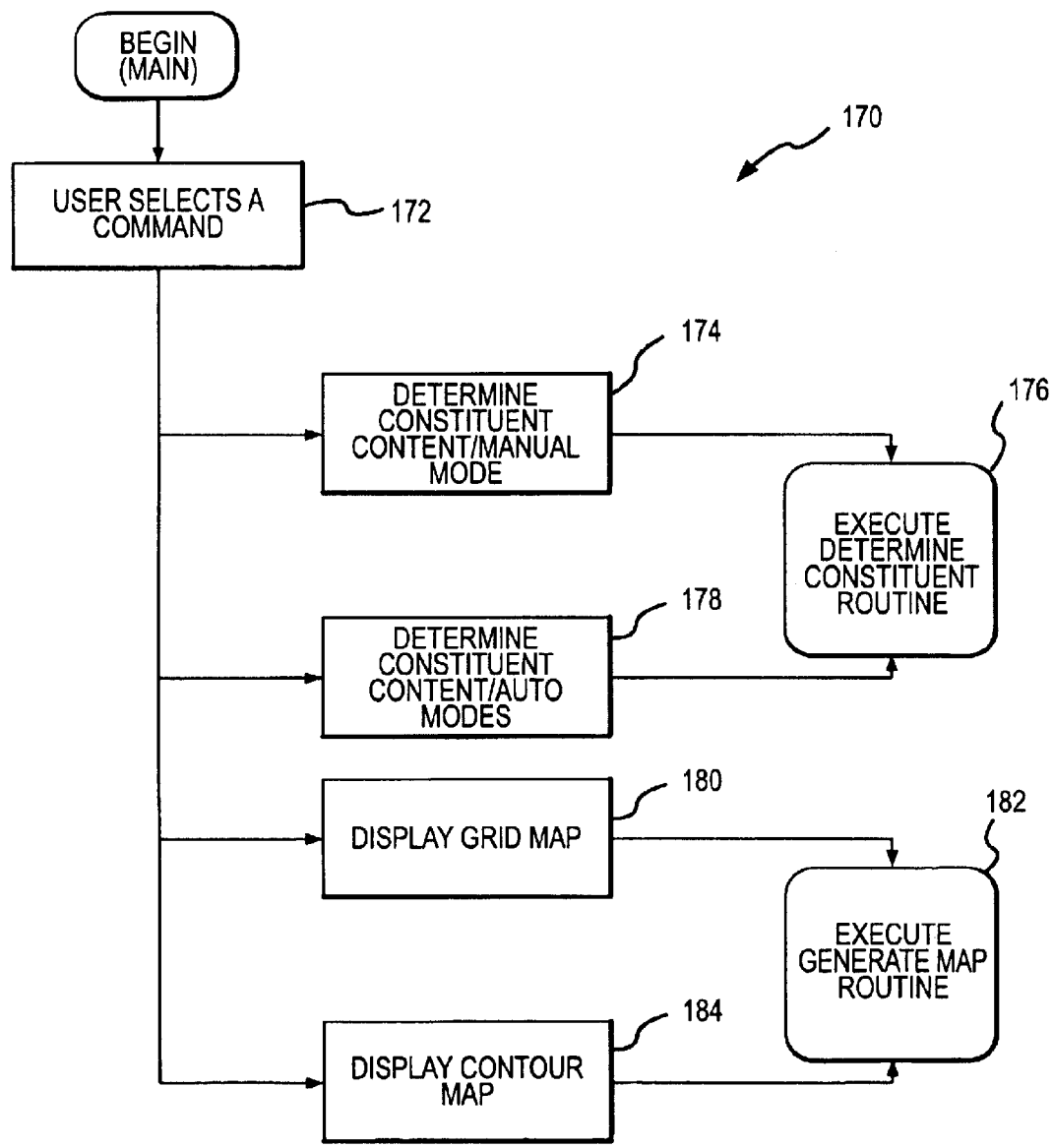
FIG. 11 is a flow chart of a main routine for processing of a signal from the optical sensor.

FIG. 10 depicts a data processing system 150 with a computer 151 illustrating exemplary hardware components of computer 70. Computer 151 may include a connection with a network 160 such as the Internet or other type of network, and it can include a wireline or wireless connection with the network. For example, if the optical sensor is used in a food processing facility, the computer may include a wireline connection with a network to transmit stored constituent data. On the other hand, if the optical sensor is used on a combine, the computer may include a wireless connection with a network to transmit the constituent data.

Computer 151 typically includes a memory 152, a secondary storage device 154, a processor 155, an input device 156, a global positioning system (GPS) 157, a display device 153, and an output device 158. A GPS is known in the art and provides approximate longitude and latitude coordinates for its geographic location based upon triangulation of signals received from GPS satellites. Memory 152 may include random access memory (RAM) or similar types of memory, and it may store one or more applications 159 for execution by processor 155. Secondary storage device 154 may include a hard disk drive, floppy disk drive, CD-ROM drive, or other types of non-volatile data storage. Processor 155 may execute applications or programs stored in memory 152 or secondary storage 154, or received from the Internet or other network 160. Input device 156 may include any device for entering information into computer 151, such as a keyboard, key pad, cursor-control device, or touch-screen. Display device 153 may include any type of device for presenting visual information such as, for example, a computer monitor, flat-screen display, or display panel. Output device 158 may include any type of device for presenting a hard copy of information, such as a printer, and other types of output devices include speakers or any device for providing information in audio form.

Computer 151 also includes in this example spectrometer 69 connected with fiber optic cable 68. Spectrometers are known in the art, and the term "spectrometer" refers to any type of component for converting a light signal into a corresponding electrical signal at various specific wavelengths. Therefore, spectrometer 69 receives the light signal from fiber optic cable 68, converts it into a corresponding analog electrical signal, and digitizes the analog signal through an analog-to-digital (A/D) converter to produce a digitized version of the raw spectral signature. The A/D conversion can be implemented as part of spectrometer 69 or as a separate component such as a controller card in computer 151. Also, spectrometer 69 can be implemented as part of computer 151 or as a separate physical component electronically linked with computer 151. Depending upon the agricultural product to be analyzed, spectrometer 69 can be calibrated to convert a range of the light signal between particular wavelengths. The range of the light signal used for prediction of protein content, as in this example, may be different for various types of agricultural products as determined through empirical evidence.

Although computer 151 is depicted with various components, one skilled in the art will appreciate that this computer can contain additional or different components. In addition, although aspects of an implementation consistent with the present invention are described as being stored in memory, one skilled in the art will appreciate that these aspects can also be stored on or read from other types of computer program products or computer-readable media, such as secondary storage devices, including hard disks, floppy disks, or CD-ROM; a carrier wave from the Internet or other network; or other forms of RAM or ROM. The computer-readable media may include instructions for controlling a computer system, such as computer 151, to perform a particular method.

Figure 12:
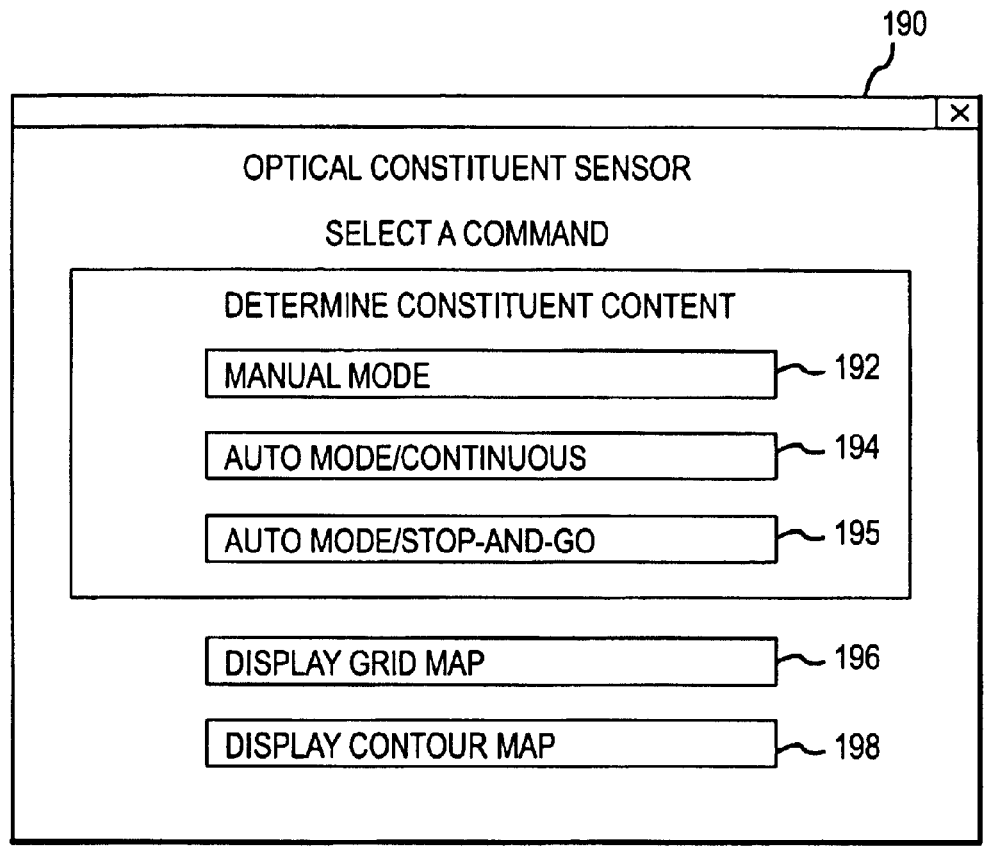
FIG. 12 is a diagram of a main screen for use with the optical sensor.
Figure 18:
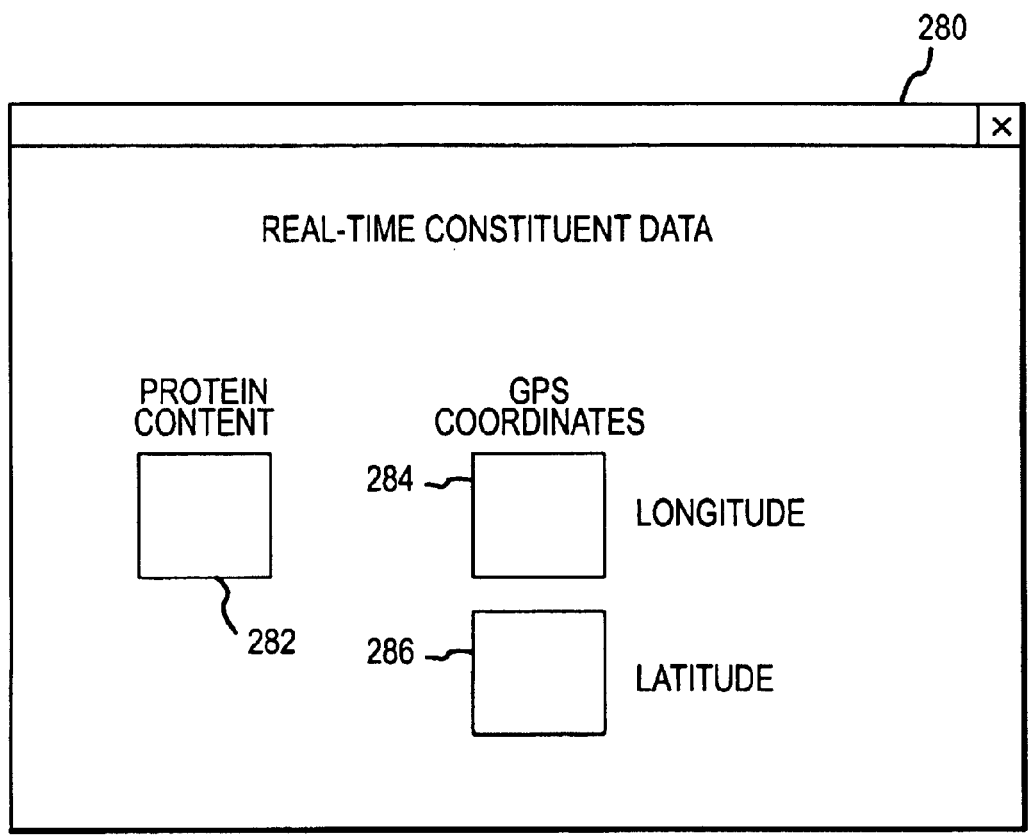
FIG. 18 is a screen for displaying real-time constituent data.

Computer 151 can display a screen through which a user interacts with the system. FIG. 12 is a diagram of a screen illustrating how a user can interact with the system, and this screen may be displayed on display devices associated with the user's computers. Computer 151 can also display a screen to present information, such as constituent data to a user, and an example of such a screen is shown in FIG. 18. The term "screen" refers to any visual element or combinations of visual elements for displaying information; examples include, but are not limited to, user interfaces on a display device or information displayed in web pages or in windows on a display device. The screens may be formatted, for example, as web pages in HyperText Markup Language (HTML), or in any other suitable form for presentation on a display device depending upon applications used to interact with the system.

The screens include various sections, as explained below, to provide information or to receive information or commands. The term "section" with respect to screens refers to a particular portion of a screen, possibly including the entire screen. Sections are selected, for example, to enter information or commands or to retrieve information or access other screens. The selection may occur, for example, by a using a cursor-control device to "click on" or "double click on" the section; alternatively, sections may be selected by entering a series of key strokes or in other ways such as through voice commands or use of a touch screen. In addition, although the screens shown in FIGS. 12 and 18 illustrate a particular arrangement and number of sections, other arrangements are possible and different numbers of sections in the screen may be used to accomplish the same or similar functions of displaying information and receiving information or commands. Also, the same section may be used for performing a number of functions, such as both displaying information and receiving a command.

The processing to support the screens is shown in the flow charts of FIGS. 11, 13, 14, 17, and 19 specifying various routines. The processing may be implemented in software, such as software modules, for execution by computer 151 or other machines.

Software Processing

FIG. 1 is a flow chart of a main routine 170 for execution by computer 70 in order to analyze constituent contents of an agricultural product and provide a visual indication of it. The main routine 170 shown in FIG. 11 may be used in conjunction with a main screen 190 shown in FIG. 12. Main screen 190 may be displayed on a corresponding display device and can be used for inputting commands into the computer. In particular, main screen 190 includes a section 192 for determining a constituent content in a manual mode, a section 194 for determining a constituent content in an automatic mode for a continuous stream of an agricultural product, a section 195 for determining a constituent content in an automatic mode for a stop-and-go stream of an agricultural product, a section 196 for displaying a grid map of constituent contents of a field, and a section 198 for displaying a contour map of constituent contents of a field.

A user may select one of these sections to enter the corresponding command. The manual mode referred to in section 192 means that the optical sensor analyzes and predicts a constituent content in response to user input. The automatic (continuous) mode referred to in section 194 means that the optical sensor, based upon a time parameter, repeatedly analyzes and predicts a constituent content of a continuous stream of the agricultural product. The automatic (stop-and-go) mode referred to in section 195 means that the optical sensor, based upon a time parameter, repeatedly analyzes and predicts a constituent content of a stop-and-go stream of the agricultural product. The stop-and-go stream refers to substantially stopping the flow of the agricultural product past the sensing window, sampling the product, and then restarting the flow of the product.

In routine 170, the user selects a command such as is shown in main screen 190 (step 172). Based upon the enter command, the system executes a corresponding routine. If the user selected section 192 for the manual mode (step 174) or one of sections 194 or 195 for the automatic modes (step 178), the system executes a determine constituent routine (step 176). If the user selected section 196 for displaying a grid map (step 180) or section 198 for displaying a contour map (step 184), the system executes a generate map routine (step 182). Main screen 190 is only one example of how a user may enter a command to the system, and a user can enter commands in a variety of ways, such as through use of a touch screen, voice command, key stroke, or peripheral device.

Figure 13:
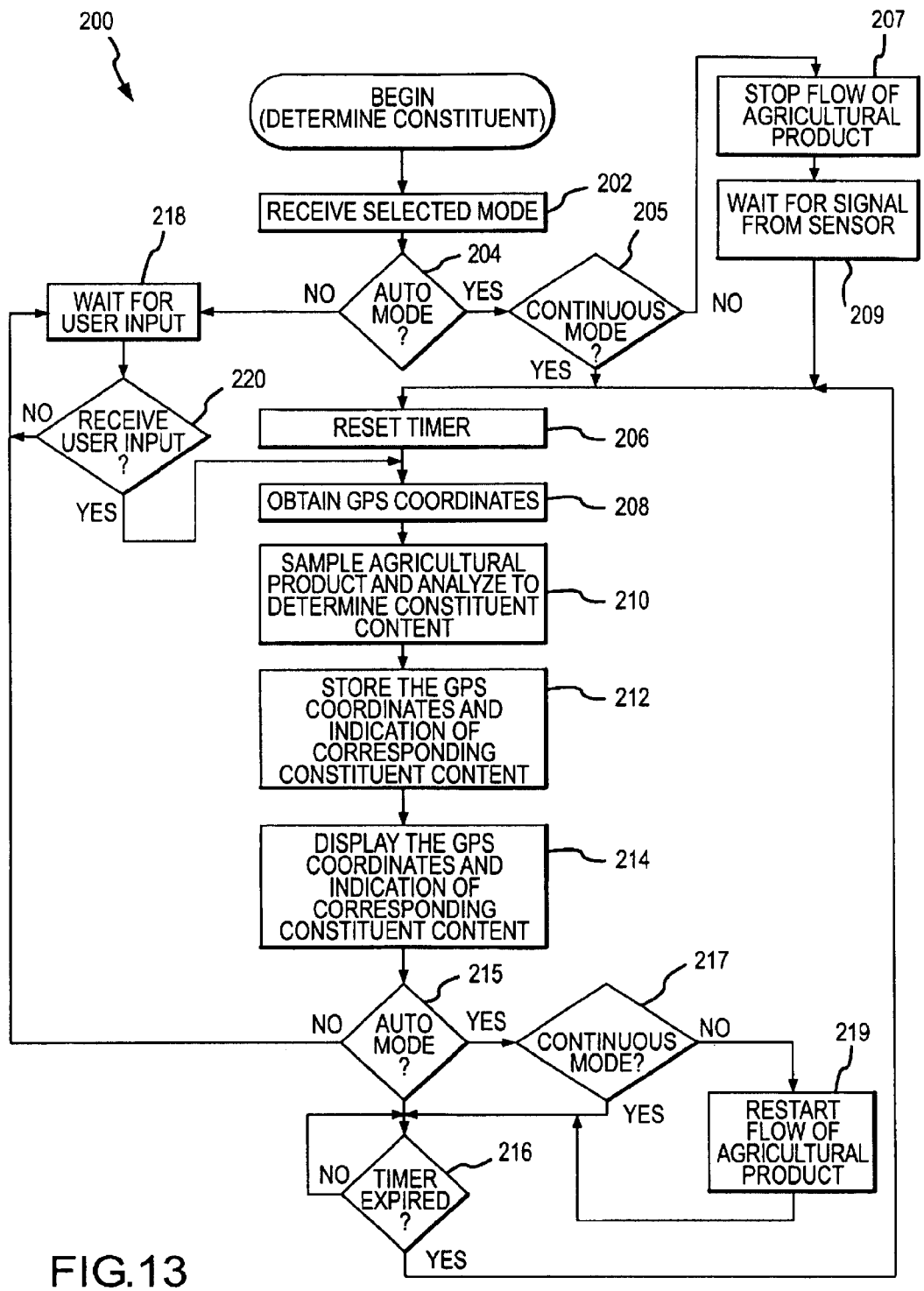
FIG. 13 is a flow chart of a determine constituent routine for use with the optical sensor.

FIG. 13 is a flow chart of a determine constituent routine 200 triggered by step 176. In routine 200, the system receives a selected mode (step 202); this mode may be determined based upon which section 192, 194, or 195 the user selected within screen 190. The system determines whether the user selected the manual or automatic mode (step 204). If the user selected the manual mode, the system waits for user input (step 218). When the system receives an appropriate user input (step 220), it analyzes the agricultural product to predict a constituent of it, as described below. Ite user input can be any type of user-entered command, either locally or remotely through network 160, to sample the agricultural product. That command can be entered through any of the exemplary user input devices provided above such as through a key stroke, touching a touch-screen, or a spoken command, or through other devices.

For the automatic mode, the system determines if the user had selected the continuous mode identified in section 194 (step 205). If the user selected the continuous mode, the system proceeds with sampling the product, as described below. If the user had selected the stop-and-go mode identified in section 195, and as determined in step 205, then the system stops the flow of agricultural product by sending an appropriate signal to control unit 47 controlling motor 48 (step 207). Once the motor is stopped, the system waits for a signal from sensor 42, indicating that the stopped flow of the agricultural product has reached the level of the sensor (step 209), which means that the agricultural product has accumulated by a sufficient amount to be present in the sensing window.

For both automatic modes, the system resets a timer for the time parameter (step 206). The time parameter determines when to repeatedly sample the agricultural product for these exemplary embodiments. The system can alternatively repeatedly sample the agricultural product based upon other input parameters. For example, it can specify particular GPS coordinates to trigger sampling. As another example, it can monitor a speed of a combine on which sensor is affixed in order to calculate, using an internal clock of computer151, when the combine travels a particular physical distance and sample the agricultural product at those distances.

The system then samples the agricultural product for any of the manual, continuous automatic, or stop-and-go automatic modes as follows. In this exemplary embodiment, the system obtains GPS coordinates from GPS sensor 157 (step 208). The system then samples the stream of agricultural product and analyzes it to predict constituent content (step 210). This step is further explained below. The system stores the GPS coordinates and an indication of the corresponding constituent content (step 212). The system may store this information in a database structure that associates GPS coordinates with the corresponding constituent contents, such as in a table or relational database form as shown in Table 1.

TABLE 1

| GPS coordinates | | |
| --- | --- | --- |
| longitude | latitude | constituent content |
| longitude value 1 | latitude value 1 | constituent content value 1 |
| longitude value 2 | latitude value 2 | constituent content value 2 |
| . . . | | |
| longitude value N | latitude value N | constituent content value N |

The system may also display the GPS coordinates and indication of the corresponding constituent content (step 214). This step permits the optional display in real-time or near real-time of constituent contents as the stream of agricultural product is analyzed. For example, as grain is harvested in the field, a combine operator may view an indication of protein content of the grain as it is being harvested. As another example, as grain or other agricultural product is moved through the assembly line of a food processing plant, an operator may view an indication of the protein content of the grain as it moves through the food-making process.

If the system is in the automatic mode (step 215), it also determines whether is in the continuous or stop-and-go automatic mode (step 217). If it is the stop-and-go mode, it restarts the flow of the agricultural product by sending an appropriate signal to control unit 47 controlling motor 48 in order to restart the motor (step 219). For both automatic modes, the system determines constituent contents at regular intervals by determining if the timer has expired (step 216). Therefore, at regular intervals, the system can sample the stream of agricultural product, predict the constituent content of it, and store an indication of that constituent content along with the GPS coordinates. If the system is in the manual mode, it returns to step 218 to wait for another user input.

This exemplary routine 200 is shown for use on a combine during harvesting of a field. However, if the optical sensor were used within a different environment, such as in a food processing facility, certain steps may not be necessary, such as the steps to obtain the GPS coordinates. As an alternative to obtaining the GPS coordinates, if the stream of agricultural product is within a food processing facility, the system could alternatively store time indications of when the stream of agricultural product was sampled and analyzed. The system could then display those times along with corresponding indications of constituent content in order to provide, for example, an indication of the consistency in the constituent content of the agricultural product as used within the food processing facility.

In addition, the resulting constituent content could be used as a signal to trigger the agricultural product being directed to different portions of a food processing facility depending upon the type of constituent required at those places. Alternatively, the indication of constituent content could be used for labeling of different types of food products produced from the agricultural product. For example, a stream of grain having a high protein content may be directed to or labeled as a high quality food product, while grain having a lower protein content could be directed to or labeled as a lower quality food product.

Figure 14:
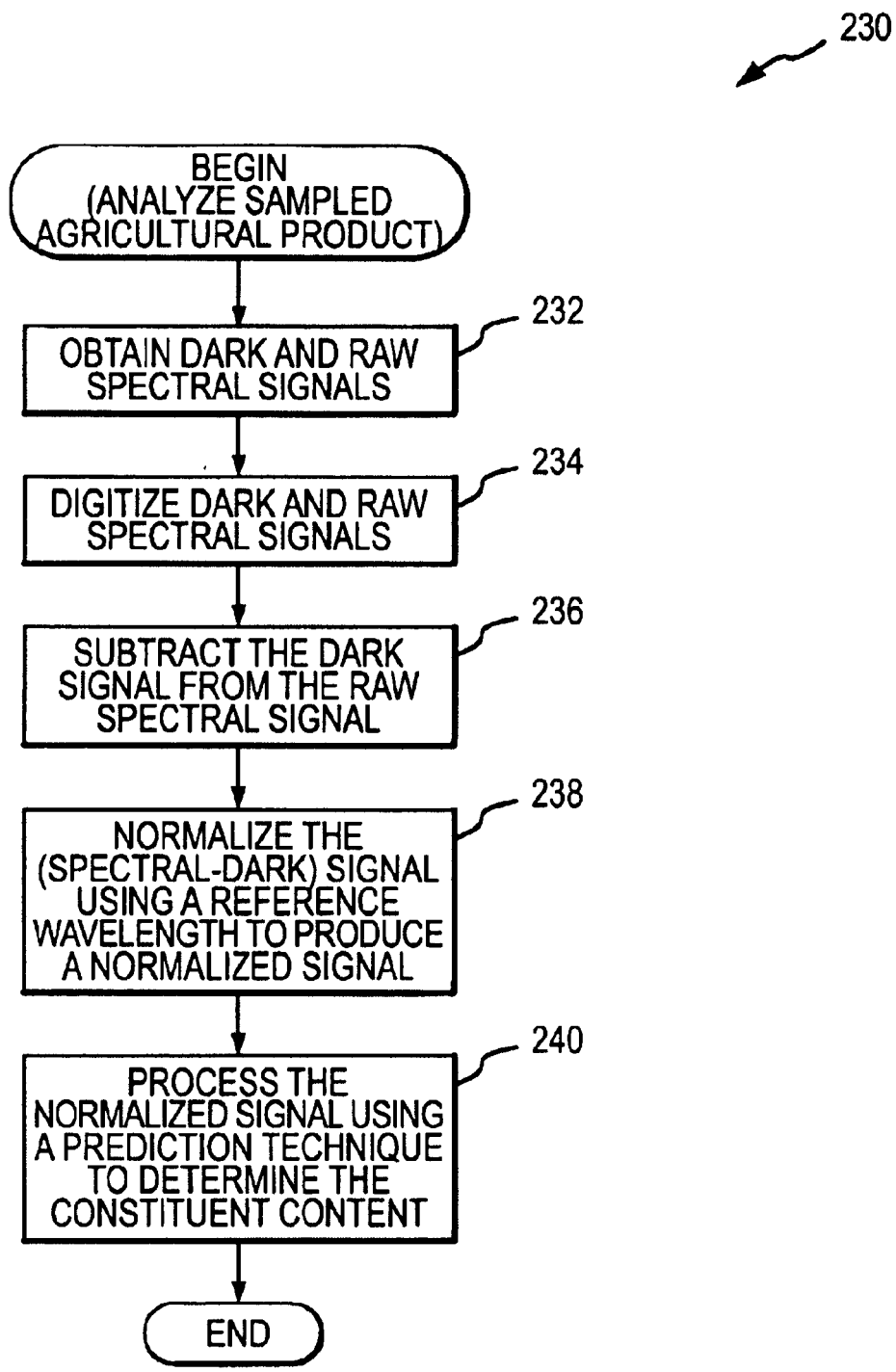
FIG. 14 is a flow chart of an analyze sampled agricultural product routine.

FIG. 14 is a flow chart of a routine or algorithm 230 for performing the analysis of the sampled agricultural product in step 210. This algorithm is a technique that allows processing of the acquired signal for predicting the constituent of the product. This technique does not require a reflectance or transmission signal of a separate standard, to process the acquired signal, as being done by standard methods. This algorithm can work with both reflectance and transmission spectral signals. This algorithm is called prediction calibration using product spectrum.

In routine 230, the optical sensor obtains the raw spectral and dark signals (step 232). The raw spectral signal is obtained from the transmitted light through the agricultural product, as received by the sensor and directed onto fiber optical cable 68. The received signal is in analog form at that point.

Figure 15:
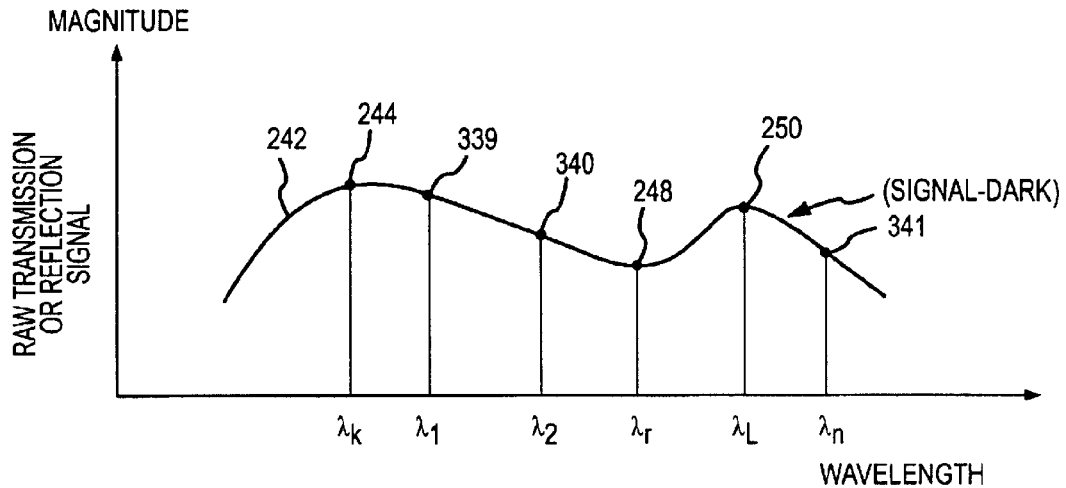
FIG. 15 is a graph illustrating spectral components of a reflected signal from the optical sensor and a reference wavelength.
Figure 16:
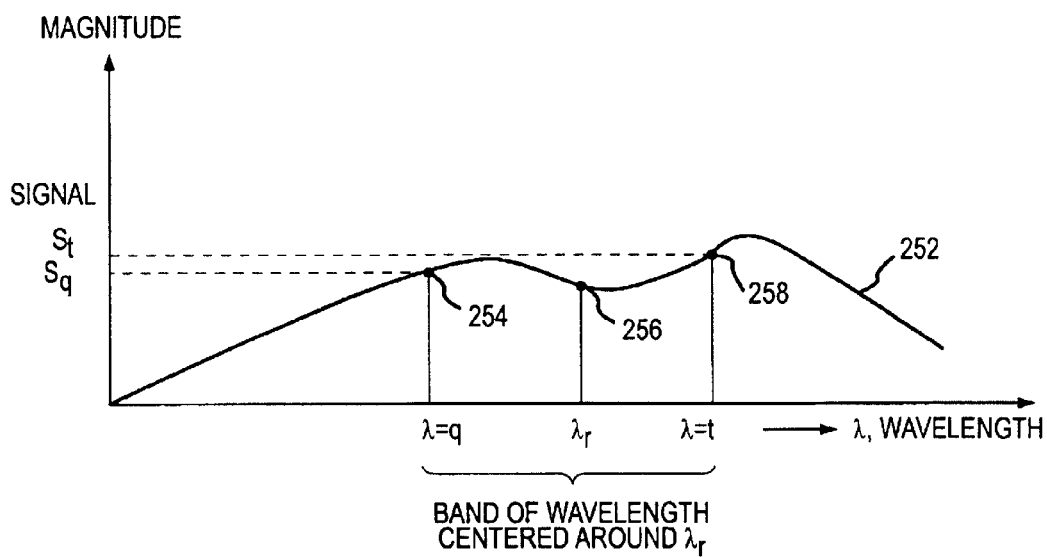
FIG. 16 is a graph illustrating spectral components of the reflected signal and a band of reference wavelengths.

FIGS. 15 and 16 are examples of a raw spectral signal 242 (with the dark signal subtracted) and various points upon it corresponding to particular wave lengths. The raw spectral signal may be analyzed between wavelengths corresponding to points 244 and 250. These wavelengths may be known in advance through various techniques to determine a spectral range required for predicting constituent content of a particular agricultural product.

A point 248 represents a particular wavelength used as a reference to normalize the data points. In particular, it may be determined based upon empirical evidence that a particular constituent is not affected by the magnitude of the waveform at a particular wavelength.

Referring again to FIG. 14, the analog signal is digitized to produce a digitized raw spectral signals (step 234). To perform processing on the digitized signal, the computer can store a particular number of the data points from the digitized signal within a table, array, or other data structure corresponding with magnitudes of the signal at certain wavelengths. In addition, the computer can store a dark signal, typically predetermined, for the signal at the corresponding wavelengths. Use of a "dark signal" is known in the art. It can also store a resulting (spectra–dark) signal as explained below. Table 2 illustrates an exemplary array of data points.

TABLE 2

| wavelength | magnitude of received signal | magnitude of dark signal | spectra - dark signal |
|---|---|---|---|
| $\lambda_k$ | magnitude value 1 | dark signal magnitude value 1 | value 1 |
| $\lambda_{k+1}$ | magnitude value 2 | dark signal magnitude value 2 | value 2 |
| ... | | | |
| $\lambda_L$ | magnitude value N | dark signal magnitude value N | value N |

Next, the dark signal is subtracted from the raw spectral signal (step 236) using, for example, equation (1).

$$[Su_\lambda]_{\lambda=k}^{\lambda=L} = (spectra - dark)_{\lambda=k, L} \quad (1)$$

The computer can perform the subtraction for each data point by retrieving each value of the digitized spectral signal and dark signal from a data structure such as shown in Table 2 and sequentially performing the subtraction. It can store the resulting values back in column four of Table 2 as shown for use in subsequent processing, or in another data structure.

Alternatively for step 236, the computer can determine an average signal for each data point. In particular, the system can take two readings of the same sample and determine the average of the sampled signal minus the dark signal. For each data point (spectra–dark) shown in equation (1), the computer determines Average_signal=[((signal1–dark)+(signal2–dark))/2]. Signal1 and signal2 represent the two raw spectral signals of the same sample for each data point. The system can also take more than two readings for each sample and determine the average based upon more than two readings. The use of an average signal for the same sample (each data point) helps to remove variations in the signal resulting from random particle size; other mathematical techniques can also be used to help remove or minimize effects of those variations.

Next, the (spectral–dark) signal is normalized using a reference wavelength to produce a normalized signal (step 238). This step can be accomplished using, for example, equation (2).

$$[Sn_\lambda]_{\lambda=k}^{\lambda=L} = \frac{[Su_\lambda]_{\lambda=k}^{\lambda=L}}{S_{\lambda d}} \quad (2)$$

where,
$Sn_\lambda$=normalized signal from $\lambda=k$ to $\lambda=L$
$\lambda_d$=normalizing wavelength $\lambda_d$
$S_{\lambda d}$=spectral signal at normalizing wavelength $\lambda_d$
$\lambda_d$ can be $\lambda_1$, or $\lambda_2$, or $\lambda_3$, ... $\lambda_n$, pr $\lambda_T$
$S_{\lambda d}$ can also be P where, P=f($\lambda_1$, $\lambda_2$, $\lambda_3$, ... $\lambda_n$)
f=any mathematical function As shown in FIG. 15, $\lambda_1$, $\lambda_2$, ... $\lambda_n$ (339, 340, 341) are wavelength(s) critical for predicting the constituent of the product. They can be wavelength(s) with highest or higher correlation with the concentration of the constituent, to be determined. As also shown in FIG. 15, $\lambda_T$ is a reference wavelength or equivalent of a band of wavelengths that does not contribute to the concentration of the desired constituent or does not have any correlations with the concentration of the desired constituent. The wavelength $\lambda_T$ could be predetermined from prior experiments, or through empirical evidence.

In equation (2), $S_{\lambda d}$ can be replaced by $S_{\lambda b}$ as shown in equation (3).

$$S_{\lambda b} = f\left([S_\lambda]_{\lambda=q}^{\lambda=t}\right), \text{ for } \lambda = q \ldots, t; \quad (3)$$

where, $S_\lambda$ = Signal at a given wavelength, $\lambda$ f=any linear and/or non-linear function, that may or may not be dependent on $\lambda$, wavelength.

A specific form of equation (2) can be obtained by using a $\lambda_T$ for $\lambda_d$ and a specific function (average) in equation (3), as shown in equation 3-A.

$$S_{\lambda b} = \sum_{\lambda=q}^{\lambda=t} S_\lambda / N, \text{ for } \lambda = q \ldots, t \quad (3\text{-A})$$

where N=number of observations corresponding to wavelength, $\lambda=q, \ldots t$.

FIG. 16 illustrates this concept further. It can be seen that, instead of using a reference wavelength, a band of wavelengths centered around the reference wavelength may be used. In particular, a spectral signal 252 may have a reference wavelength at point 256. In order to account for minor variations in the intensity at point 256 based on other factors apart from constituent content, the system may use an average magnitude value of a band of wavelengths between points 254 and 258 to normalize the spectral signal.

With this routine, the reference wavelength is known in advance. The magnitude at the reference wavelength can thus be used to normalize the spectral signal and predict constituents in real-time or near real-time without the need to obtain separate reference signals upon every sampling of the agricultural product.

By using a data structure, the computer can retrieve the values of the data points for each wavelength and compute the processed signal ($S_{n\lambda}$). It can also store the resulting processed signal values in the same table or other data structure, as illustrated by Table 3.

TABLE 3

| wavelength | processed signal |
|---|---|
| $\lambda_k$ | value 1 |
| $\lambda_2$ | value 2 |
| ... | |
| $\lambda_L$ | value N |

The system then processes the normalized signal using, for example, a standard prediction technique known in the art to determine the constituent content (step 240), as explained below.

Additional processing can be performed on the data points as well. In addition to the processing occurring through equation (1), the (spectra–dark) signal can be processed in any linear or non-linear way before the normalizing step 238. Also, the normalized signal can be processed in any linear or non-linear way in addition the normalizing occurring through equation (2).

Figure 17:
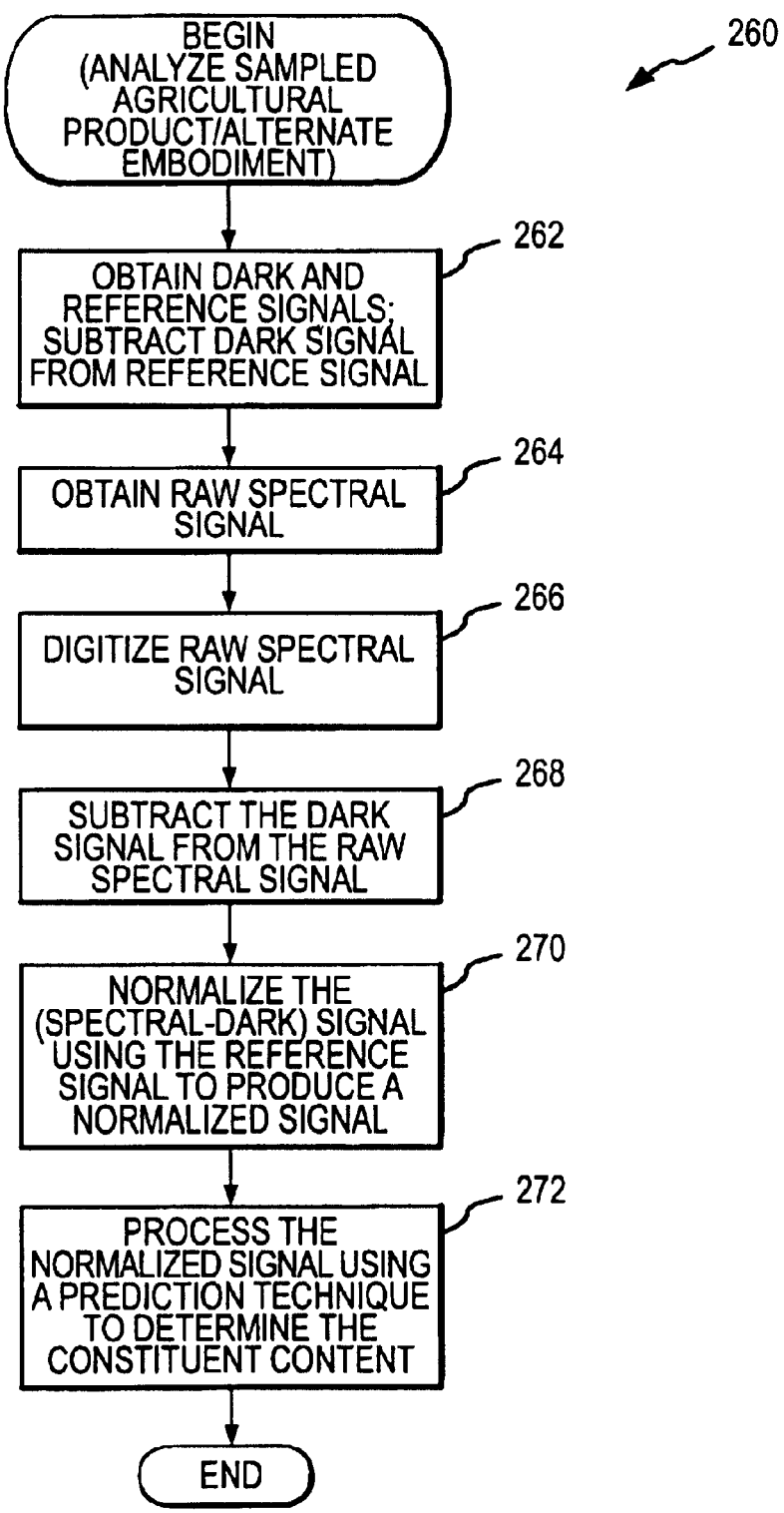
FIG. 17 is a flow chart of a method for analyzing a sampled agricultural product according to an alternate embodiment.

FIG. 17 shows a flow chart for two other routines or algorithms 260 that will also eliminate the need for obtaining reflectance or transmittance signals of separate standards and thus are alternate embodiments for analyzing the spectral signal to determine the constituents of the agricultural product in step 210. In both techniques (alternate embodiments), the system first obtains a reference signal and dark signal (step 262). To obtain the reference signal, a separate physical standard is not required. These two techniques are called (1) prediction calibration using specific wavelength and (2) prediction calibration using illumination spectrum.

The technique "prediction calibration using specific wavelength" involves receiving the radiation transmitted without any agricultural product present in the optical sensing window and using the magnitude of that received radiation at specific wavelengths. The other technique, "prediction calibration using illumination spectrum," involves receiving transmitted radiation with a gating mechanism or a mechanism to reduce light intensity while no agricultural product is present in the optical sensing window and using the magnitude of that received radiation. A gating mechanism could include any device to block or attenuate at least a portion of the transmitted radiation and examples include a mesh screen. The mechanism to reduce light intensity could also include any method to decrease the intensity of the illumination source (light) by changing the supplied voltage or current. In this technique, a gating mechanism or mechanism to reduce light intensity is only used to obtain the reference signal (step 262). For obtaining the spectral signal of the product sample (step 264), a gating mechanism or mechanism to reduce light intensity is not used.

For both of these techniques, the apparatus can include a valve or other mechanism to block the stream of the agricultural product passed through the optical sensing window in order to obtain the reference signal.

The system can obtain the reference signal through these or other methods at various times. It can obtain the reference signal upon each irradiation and analysis of the agricultural product as shown in routine 260. Alternatively, it can obtain the signal other than during every analysis. For example, it may obtain the reference signal once for the analysis of an entire field of the agricultural product during harvesting. It may also obtain the reference signal periodically based upon, for example, a user-defined time parameter.

The system then performs essentially the same steps as in routine 230 except that it is uses the reference signal to normalize the spectral signal. In particular, the system obtains the raw spectral signal through the stream of agricultural product (step 264), digitizes it to produce a digital signal having a series of data points corresponding to particular wavelengths (step 266), subtracts the dark signal from the raw spectral signal (step 268), and normalizes the (spectral–dark) signal using the reference signal in order to produce a normalized signal (step 270). The processing for steps 268 and 270 depend upon a particular application and the type of reference signal used.

For the prediction calibration using specific wavelength method, equation (4) can be used to perform steps 268 and 270.

$$S_c = \log_{10}\left[\frac{\left\{\frac{I_{t\lambda 2} - dark}{I_{t\lambda 1} - dark}\right\}}{\left\{\frac{I_{o\lambda 2} - dark}{I_{o\lambda 1} - dark}\right\}}\right] \quad (4)$$

In equation (4) $\lambda_1$, $\lambda_2$ ... are wavelengths critical for predicting the constituent of the agricultural product, $I_{t\lambda 2}$ is the magnitude of the transmitted radiation (raw spectral signal) at wavelength $\lambda_2$ with the agricultural product present in the sampling window, $I_{t\lambda 1}$ is the magnitude of transmitted radiation (raw spectral signal) at wavelength $\lambda_1$ with the agricultural product present in the sampling window, $I_{o\lambda 2}$ is the magnitude of the received radiation at reference wavelength $\lambda_2$ (reference signal) with no agricultural product present in the sampling window, $I_{o\lambda 1}$ is the magnitude of the received radiation at reference wavelength $\lambda_1$ (reference signal) with no agricultural product present in the sampling window.

For the prediction calibration using illumination spectrum method, equation (5) can be used to perform steps 268 and 270.

$$[S n_\lambda]_{\lambda=k}^{\lambda=L} = \frac{[T_\lambda]_{\lambda=k}^{\lambda=L} - darksignal}{[R_\lambda]_{\lambda=k}^{\lambda=L} - darksignal} \quad (5)$$

In equation (5), $$[R_\lambda]_{\lambda=k}^{\lambda=L}$$

is the reference signal obtained for wavelengths k to L with the gating mechanism but no agricultural product present, and $$[T_\lambda]_{\lambda=k}^{\lambda=L}$$

is the transmitted raw spectral signal obtained for wavelengths k to L without the gating mechanism but with the agricultural product present.

For step 268, the computer can alternatively determine an average signal for each data point and use that average in the equations as described above. In particular, the system can take two readings of the same sample and determine the average of the sampled signal minus the dark signal. For each data point, shown in equation (4) or (5), the computer determines Average_signal=[((signal1−dark)+(signal2−dark))/2]. Signal1 and signal2 represent the two raw spectral signals of the same sample for each data point. The system can also take more than two readings for each sample and determine the average based upon more than two readings. The use of average signal for each data point helps to remove variations in the signal resulting from random particle size; other mathematical techniques can also be used to help remove or minimize effects of those variations.

The system processes the normalized signal using, for example, a standard prediction technique known in the art to determine the constituent content (step 272).

The standard techniques for steps 240 and 272 usually involve linearizing the data, which can be accomplishing by calculating a logarithm of the data output from step 238 for routine 230 or step 270 for the alternate embodiments of routine 260. The logarithm involves calculating $S_L = \log_{10}(S_{n\lambda})$ for ale each of the data points. The signal $S_c$ (equation (4)) was already linearized. The set of linearized data points $S_L$ or $S_c$ can then be processed according to standard techniques for the particular constituent desired and type of agricultural product sampled. For example, to calculate the protein content of barley, oats, rye, triticale, and wheat of all classes, the data points $S_L$ or $S_c$ can be processed according to the American Association of Cereal Chemists (AACC) method 39-10, and to calculate the protein content of whole-grain wheat, the data points $S_L$ or $S_c$ can be processed according to AACC method 39-25. AACC methods 39-10 and 39-25 are known in the art. These standard techniques can involve statistical analysis of the data points, which can be accomplished using conventional software for performing the particular statistical analysis functions on the data.

For other types of constituents or agricultural products, other standard techniques can be used to process the data points $S_L$ or $S_c$. Accordingly, once of the data points are obtained after step 238 in routine 230 and step 270 in routine 260, those data points can be processed in steps 240 and 272 according to a variety of standard and known techniques for a variety of constituents and agricultural products. The data points can also be stored for later processing or for processing according to varying standards and statistical techniques.

As an example, the $S_L$ data points were tested and processed as follows for determining protein content of wheat. Two prediction calibration techniques were used. They were (1) prediction calibration using product spectrum and (2) prediction calibration using illumination spectrum. This experiment also was used to validate the performance of these two prediction calibration techniques or algorithms. Using GRAM-32, version 5.03, a software program from Galactic Industries, N.H., the signal $S_L$ was further processed as follows: offset correction was performed on the y-axis with the option of "set point to zero"; the signal was smoothed using "binomial smoothing" with the number of points equal to four; the data was reduced by a factor of six-to-one using an averaging technique under the interpolation option of the software; and a second derivative was calculated with a gap value equal to twenty.

Randomly selected wheat samples (501 samples) were used and their raw signals were obtained using the sensor system. After the processing of $S_L$, 125 data points represented each spectral signal of every wheat sample. For the prediction calibration using product spectrum technique, there were 420 training and 81 test data sets. For the prediction calibration using illumination spectrum technique, there were 420 training and 80 test data sets. For purposes of the testing, signals were acquired in the stop-and-go mode. Each sample was put into the sensing window two times and two spectral signals were acquired for each sample; the average of the two signals was used.

The data were then further processed using Principle Component Regression (PCR) and Partial Least Square (PLS) to develop a prediction model, using SAS software from Statistical Analysis Software, N.C. The prediction model predicted the protein content percentage for the wheat sample. Though the actual protein contents of wheat samples are determined by using standard reference methods such as the Kjeldahl (AACC 39-25) method, in this study a separate commercial laboratory scale NIR analyzer (model Infratec 1226 grain analyzer, FOSS, Eden Prairie, MN) was used to determine the protein content of the wheat sample. Because this instrument is also widely used for determining protein content, the obtained protein contents were considered as actual protein contents of wheat samples. The protein contents determined by the commercial NIR instruments were compared with the protein contents predicted by the system and the models. This testing illustrates only one example of processing the data points, and other conventional techniques and software programs can be used.

FIG. 18 is a diagram of a screen 280 for displaying in real-time or near real-time GPS coordinates and corresponding constituent content, in this example protein, in step 214 in routine 200. In particular, a screen 280 may be displayed on a display device and presented to an operator during analysis of the stream of agricultural product. It includes a section 282 for providing an indication of protein content such as a percentage or other numerical indication. It also includes sections 284 and 286 for displaying, respectively, longitude and latitude coordinates providing an indication of the approximate geographic location of the agricultural product corresponding to the displayed protein content. Therefore, the screen can be displayed in the cab of a combine during harvesting of an agricultural product. It can also be displayed on a display device at a location in a food processing facility where the stream of grain is analyzed, although it could display a time indication rather than GPS coordinates for implementation in a food processing facility.

Figure 19:
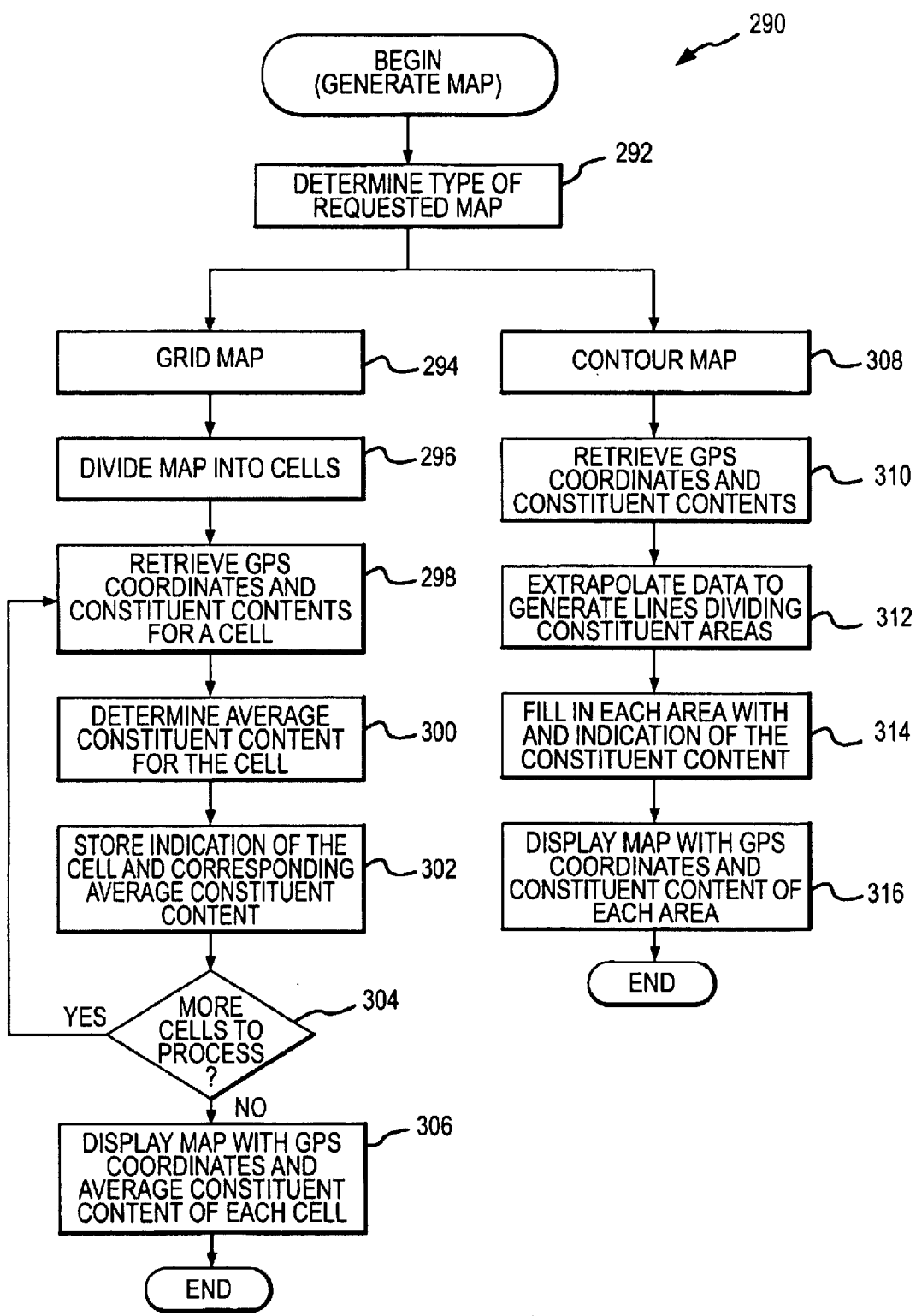
FIG. 19 is a flow chart of a generate map routine for providing a visual indication of protein content within a field of an agricultural product.

FIG. 19 is a flow chart of a generated map routine 290 for generating a visual map of constituent content among a field of an agricultural product. Routine 290 may be triggered by user's selection of sections 196 or 198 in main screen 190 for generating and displaying a map. In routine 290, the system determines the type of requested map (step 292). This may be accomplished by determining which section the user selected in main screen 190 for obtaining a map.

Figure 20:
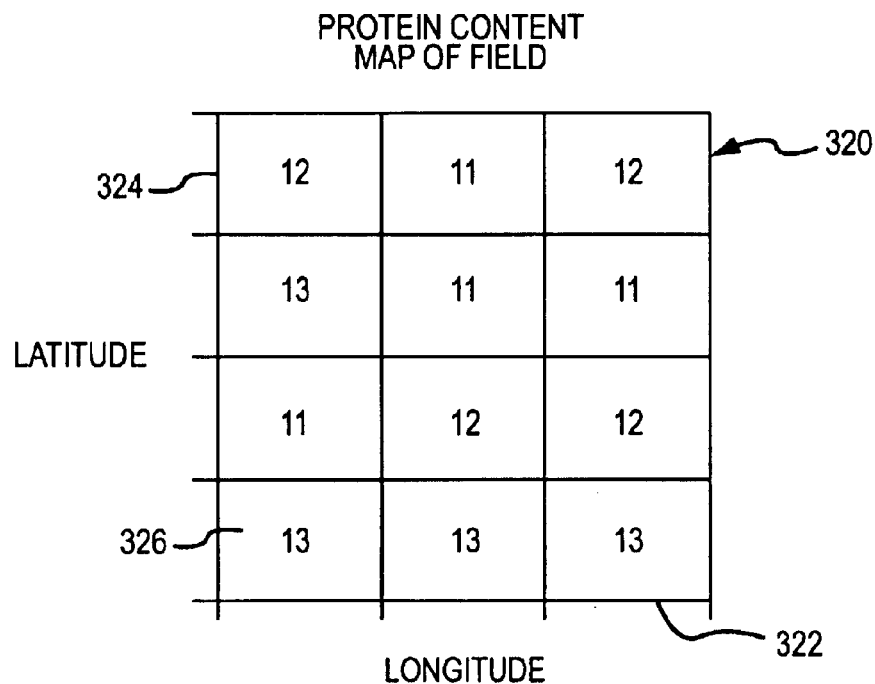
FIG. 20 is an example of a grid map illustrating protein content throughout a field of an agricultural product.
Figure 21:
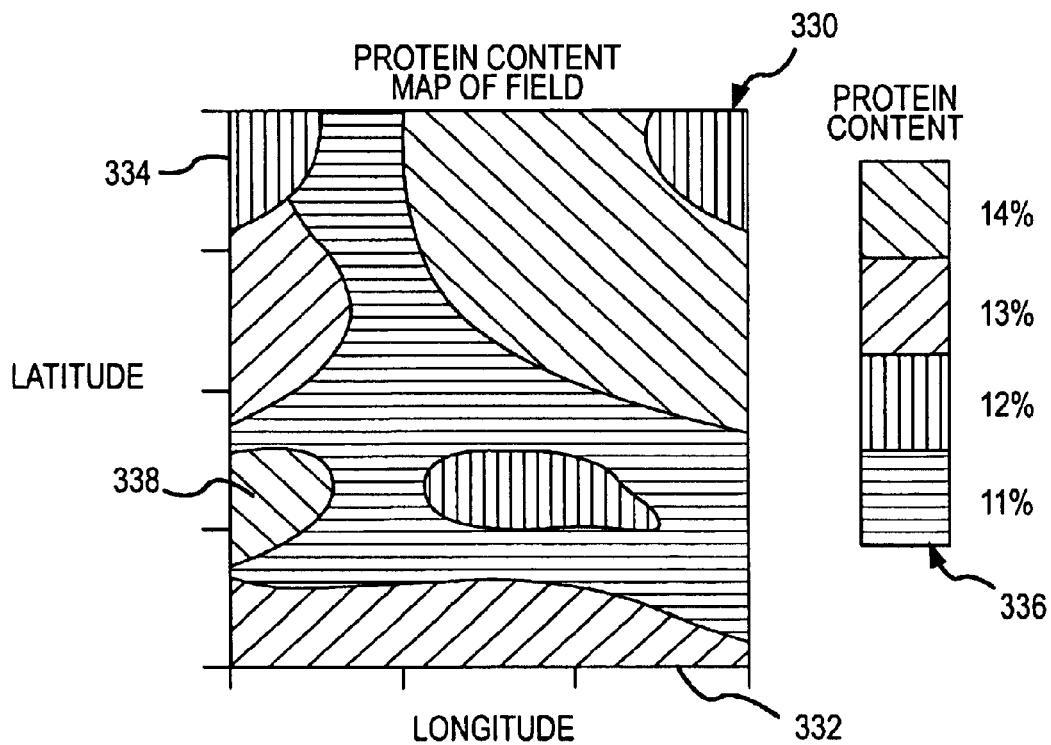
FIG. 21 is an example of a contour map illustrating protein content throughout a field of an agricultural product.

FIGS. 20 and 21 illustrate, respectively, examples of a grid map and a contour map for providing a visual indication of protein content or other constituent among a field of an agricultural product. In a grid map 320 in FIG. 20, the map includes a first axis 322 for displaying an indication of longitude coordinates, and a second axis 324 for displaying an indication of latitude coordinates. The latitude and longitude coordinates are divided into a plurality of cells, such as cell 326, and an indication of protein content is displayed for each cell. The indication of protein content may be a number indicating a percentage of protein content within the agricultural product for that section of the field, or could be some other type of indication.

FIG. 21 illustrates a contour map 330 providing another way of indicating protein content of a field. Contour map 330 includes a first axis 332 providing longitude coordinates, and a second axis 334 providing latitude coordinates. Among those longitude and latitude coordinates various indications are provided for different protein content within the field. For example, a section 338 provides an indication of one level of protein content. The contour map may be associated with a key 336 indicating which visual indications correspond with which protein content. Although various types of cross-hatching are illustrated for indicating protein content, other types of visual indication may be provided, such as different colors or shades.

Referring back to FIG. 19, grid map 320 and contour map 330 are generated in routine 290 as follows. For the contour map, as determined in step 308, the system retrieves the GPS coordinates and corresponding constituent contents from a database in memory such as is shown in Table 1 (step 310). The system extrapolates the data to generate lines dividing constituent areas within a map of the field (step 312). Data extrapolation techniques are known in the art. Each area is filled in with an indication of constituent content, such as using different colors, cross-hatching or shadings (step 314). The system then displays the map with the GPS coordinates and constituent content of each area (step 316), and the system may also store the map in order to avoid having to repeatedly generate it.

If the user had selected the grid map, as determined in step 294, the system divides the map into cells (step 296). Each cell may be indicated by the corresponding GPS coordinates within that cell. The system retrieves GPS coordinates and constituent contents for a cell from a database in memory such as is shown in Table 1 (step 298). The average constituent content is then determined for the cell (step 300). The average may be determined by adding all the constituent contents within that cell and dividing by the total number of samples for that cell. The system stores an indication of the cell and corresponding constituent content (step 302). It then determines if more cells exist to process (step 304). If so, it repeats step 298, 300 and 302 to determine an average constituent content for the next cell. When all cells have been processed, the system displays the grid map with the GPS coordinates and average constituent content of each cell (step 306), and it may also store the grid map to avoid having to repeatedly generate it.

The grid map and contour map may be displayed on a display device associated with computer 70 or printed out in bard copy form.

While the present invention has been described in connection with an exemplary embodiment, it will be understood that many modifications will be readily apparent to those skilled in the art, and this application is intended to cover any adaptations or variations thereof. For example, different types of materials for the device, and various types of software algorithms for processing the signal resulting from irradiation of the agricultural product, may be used without departing from the scope of the invention. This invention should be limited only by the claims and equivalents thereof.

What is claimed is:

1. An apparatus for measuring a constituent content of an agricultural product, comprising:

a device for forming a stream of the agricultural product;

an optical sensing window in the device allowing passage of radiation from a radiation source to pass through the stream of agricultural product to a receiver, the optical sensing window being configured, in comparison to the device, to provide a narrower passageway for the stream of agricultural product to provide for a more uniform consistency in the stream of agricultural product;

a radiation source for irradiating the stream of the agricultural product as the stream of the agricultural product passes through the optical sensing window;

a receiver for receiving radiation transmitted from the radiation source through the stream of agricultural product and the optical sensing window, and for converting the received radiation into a corresponding electrical signal; and a computer, coupled to the receiver, for receiving the electrical signal and for processing the electrical signal to generate data for use in determining a constituent content of the agricultural product.

2. The apparatus of claim 1 wherein the receiver includes:

a fiber optic cable;

a sensor head for receiving the radiation transmitted from the radiation source through the stream of agricultural product and the optical sensing window, and for focusing the received radiation onto the fiber optic cable; and a spectrometer, coupled to the fiber optic cable, for converting the received radiation into the corresponding electrical signal.

3. The apparatus of claim 2 wherein the fiber optic cable comprises a single fiber optic cable.

4. The apparatus of claim 2 wherein the sensor bead includes:

a fiber optic probe coupled to the fiber optic cable; and a plurality of optical lenses positioned between the optical sensing window and the fiber optic cable for focusing the received radiation onto the fiber optic probe.

5. The apparatus of claim 1, further including a housing for containing the device, the radiation source, the optical sensing window, and the receiver.

6. The apparatus of claim 5, further including a fan mounted within the housing.

7. The apparatus of claim 1, further including an inlet, coupled to the device, for attachment to a source providing the agricultural product.

8. The apparatus of claim 7 wherein the inlet is configured to receive the agricultural product from a combine.

9. The apparatus of claim 1 wherein the device receives the agricultural product from a grin pipe.

10. The apparatus of claim 1 wherein the optical sensing window includes:

an inner wall;

an outer wall; and a pair of side walls, wherein the inner wall, the outer wall, and the pair of side walls are joined to form a passageway for the agricultural product.

11. The apparatus of claim 10 wherein:

the inner wall is formed from an optically transparent material; and the outer wall and the pair of side walls are formed from an opaque material.

12. The apparatus of claim 11 wherein the inner wall includes:

a front planar section; and a pair of curved edges.

13. The apparatus of claim 10 wherein the outer wall includes a transparent aperture for permitting the radiation to pass through the stream of the agricultural product and to the receiver.

14. A method for measuring constituent contents of an agricultural product, comprising:

forming a stream of the agricultural product;

passing the stream of the agricultural product through an optical sensing window allowing passage of radiation from a radiation source to pass through the stream of agricultural product to a receiver, the optical sensing widow being configured, in comparison to the device, to provide a narrower passageway for the stream of agricultural product to provide for a more uniform consistency in the stream of agricultural product;

irradiating the stream of the agricultural product as the stream of the agricultural product passes through the optical sensing window;

receiving radiation transmitted from the radiation source through the stream of agricultural product and the optical sensing window, and converting the received radiation into a corresponding electrical signal; and receiving the electrical signal and processing the electrical signal to generate data for use in determining a constituent content of the agricultural product.

15. The method of claim 14 wherein the receiving radiation step includes:

receiving the radiation transmitted through the stream of the agricultural product and focusing the received radiation onto a fiber optic cable; and converting the received radiation from the fiber optic cable into the corresponding electrical signal.

16. The method of claim 15 wherein the receiving the radiation step includes focusing the received radiation onto a single fiber optic cable.

17. The method of claim 14 wherein the receiving radiation step includes using a plurality of optical lenses for focusing the received radiation onto a fiber optic probe coupled to the fiber optic cable.

18. The method of claim 14, further including providing an inlet for attachment to a source providing the agricultural product.

19. The method of claim 18 wherein the providing step includes configuring the inlet to receive the agricultural product from a combine.

20. The method of claim 13, further including receiving the agricultural product from a grain pipe.

21. A method for converting a light signal into an electrical signal for use in predicting a constituent content of an agricultural product, comprising:

receiving a light signal from an agricultural product;

converting the light signal into an electrical signal;

digitizing the electrical signal to produce a plurality of data points; and normalizing the data points using a reference signal value to produce a plurality of normalized data points, the normalized data points having values related to a constituent content of the agricultural product, wherein the reference signal value is related to a magnitude at a wavelength of the light signal substantially unaffected by the constituent content.

22. The method of claim 21 wherein the normalizing step includes using, as the reference signal value, a value derived from the magnitude using a mathematical function.

23. The method of claim 21 wherein the normalizing step includes using as the reference signal value a value related to magnitudes at a plurality of wavelengths including the wavelength of the light signal substantially unaffected by the constituent content.

24. The method of claim 21 wherein the normalizing step includes using as the reference signal value an average magnitude value of a range of magnitude values at a pair of wavelengths centered around the reference wavelength.

25. The method of claim 21, further including predicting protein content of the agricultural product using the plurality of normalized data points.

26. The method of claim 21, further including:

receiving geographical coordinates corresponding with a geographical location of the agricultural product; and associating the geographical coordinates with the constituent content of the agricultural product.

27. The method of claim 26, further including:

receiving a plurality of geographical coordinates corresponding with geographical locations of a plurality of agricultural products for which the constituent contents are predicted using the method; and associating the plurality of geographical coordinates with the constituent contents of the plurality of agricultural products.

28. The method of claim 27, further including generating a map of the constituent content of the agricultural products using the plurality of geographical coordinates and the associated constituent contents.

29. The method of claim 28 wherein the generating step includes generating a grid map.

30. The method of claim 28 wherein the generating step includes generating a contour map.

31. The method of claim 21, further including calculating average values for the data points and wherein the normalizing stop includes normalizing the average values.

32. The method of claim 21, further including linearizing the normalized data points.

33. The method of claim 32 wherein the linearizing step includes calculating a logarithm of each of the data points.

34. The method of claim 21 wherein the receiving step includes receiving the light signal from moving stream of the agricultural product.

35. The method of claim 21 wherein the receiving step includes receiving the light signal from a stopped stream of the agricultural product.

36. A method for converting a light signal into an electrical signal for use in predicting a constituent content of an agricultural product, comprising:

receiving a light signal from an agricultural product;

converting the light signal into an electrical signal;

digitizing the electrical signal to produce a plurality of data points; and normalizing the data points using a reference signal value to produce a plurality of normalized data points, the normalized data points having values related to a constituent content of the agricultural product, wherein the reference signal value corresponds with a magnitude of a received light signal at a specific wavelength without being transmitted through the agricultural product.

37. A method for converting a light signal into an electrical signal for use in predicting a constituent content of an agricultural product, comprising:

receiving a light signal from an agricultural product;

converting the light signal into an electrical signal;

digitizing the electrical signal to produce a plurality of data points; and normalizing the data points using a reference signal value to produce a plurality of normalized data points, the normalized data points having values related to a constituent content of the agricultural product, wherein the reference signal value corresponds with a magnitude of a received light signal transmitted through a gating mechanism and without being transmitted through the agricultural product.

38. An apparatus for measuring a constituent content of an agricultural product, comprising:

a device for forming a stream of the agricultural product;

an optical sensing window in the device for passing the stream of the agricultural product;

a radiation source contained within the housing for irradiating the stream of the agricultural product as the stream of the agricultural product passes through the optical sensing window;

a receiver for receiving radiation transmitted through the stream of the agricultural product and for converting the received radiation into a corresponding electrical signal; and a computer, coupled to the receiver, for receiving the electrical signal and for processing the electrical signal to generate data for use in determining a constituent content of the agricultural product, the computer operating to:

digitize the electrical signal to produce a plurality of data points; and normalize the data points using a reference signal value to produce a plurality of normalized data points, the normalized data points having values related to a constituent content of the agricultural product, wherein the reference signal value is related to a magnitude at a wavelength of the light signal substantially unaffected by the constituent content.

39. The apparatus of claim 38 wherein the computer operates to use, as the reference signal value, a value derived from the magnitude using a mathematical function.

40. The apparatus of claim 38 wherein the computer operates to use as the reference signal value a value related to magnitudes at a plurality of wavelengths including the wavelength of the light signal substantially unaffected by the constituent content.

41. The apparatus of claim 38 wherein the computer operates to use as the reference signal value an average magnitude value of a range of magnitude values at a pair of wavelengths centered around the reference wavelength.

42. The apparatus of claim 38 wherein the computer operates to predict protein content of the agricultural product using the plurality of normalized data points.

43. The apparatus of claim 38 wherein the computer operates to normalize the data points selectively using one of the following plurality of reference signal values: a magnitude at a wavelength of the light signal substantially unaffected by the constituent content, a magnitude of a received light signal without being transmitted through the agricultural product at specific wavelengths, or a magnitude of a received light signal transmitted through a gating mechanism and without being transmitted through the agricultural product.

* * * * *